United States Patent
Kawase

(10) Patent No.: US 10,058,677 B2
(45) Date of Patent: Aug. 28, 2018

(54) BALLOON CATHETER

(71) Applicant: TERUMO CLINICAL SUPPLY CO., LTD., Kakamigahara-shi, Gifu (JP)

(72) Inventor: Tatsuya Kawase, Ichinomiya (JP)

(73) Assignee: TERUMO CLINICAL SUPPLY CO., LTD., Kakamigahara-Shi, Gifu (JP)

( * ) Notice: Subject to any disclaimer, the term of this patent is extended or adjusted under 35 U.S.C. 154(b) by 0 days.

(21) Appl. No.: 14/820,283

(22) Filed: Aug. 6, 2015

(65) Prior Publication Data
US 2015/0343183 A1    Dec. 3, 2015

Related U.S. Application Data

(63) Continuation of application No. PCT/JP2013/052925, filed on Feb. 7, 2013.

(51) Int. Cl.
*A61M 25/10* (2013.01)
*A61M 25/00* (2006.01)

(52) U.S. Cl.
CPC ........ *A61M 25/003* (2013.01); *A61M 25/104* (2013.01); *A61M 2025/0039* (2013.01);
(Continued)

(58) Field of Classification Search
CPC ...... A61M 25/1025; A61M 2025/1061; A61M 25/0054; A61M 25/1002;
(Continued)

(56) References Cited

U.S. PATENT DOCUMENTS 5,156,594 A * 10/1992 Keith ................ A61M 25/0662
604/103.09
5,522,818 A   6/1996 Keith et al.
(Continued)

FOREIGN PATENT DOCUMENTS

CN    1322145 A    11/2001
CN    102793964 A    11/2012
(Continued)

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA/237) dated Aug. 11, 2015, by the International Bureau of WIPO in corresponding International Application No. PCT/JP2013/052925. (8 pages).
(Continued)

*Primary Examiner* — Theodore Stigell
(74) *Attorney, Agent, or Firm* — Buchanan Ingersoll & Rooney PC

(57) ABSTRACT

A balloon catheter has an inner tube having a first lumen, an outer tube part coaxial with the inner tube and forming a second lumen between the outer tube part and an outer surface of the inner tube, and a balloon part having a front end portion fixed to a front end portion of the inner tube and an inside communicating with the second lumen. The balloon part has a bulged portion, having an expansion forming mode formed in advance, which is elastically deformable beyond the expansion forming mode by an expansion liquid injected thereinto. The outer tube part has a front side sleeve portion extending from a rear end portion of the bulged portion of the balloon part to a proximal end of the outer tube part, integrally formed with the balloon part using the same material as that of the balloon part, and substantially non-expandable.

18 Claims, 15 Drawing Sheets

(52) U.S. Cl.
CPC ............... *A61M 2025/0059* (2013.01); *A61M 2025/1052* (2013.01)

(58) Field of Classification Search
CPC ........ A61M 2025/1004; A61M 25/104; A61M 25/003; A61M 2025/1052
See application file for complete search history.

(56) References Cited

U.S. PATENT DOCUMENTS

| | | | |
|---|---|---|---|
| 6,613,066 B1 | 9/2003 | Fukaya et al. | |
| 2006/0079727 A1* | 4/2006 | Chernomorsky . | A61M 25/1002 600/3 |

FOREIGN PATENT DOCUMENTS

| | | | |
|---|---|---|---|
| JP | 09-10314 | A | 1/1997 |
| JP | 10-511873 | A | 11/1998 |
| JP | 2933389 | B2 | 5/1999 |
| JP | 2000-217923 | A | 8/2000 |
| JP | 2002-291900 | A | 10/2002 |
| JP | 2005-103120 | A | 4/2005 |
| JP | 2008-264118 | A | 11/2008 |
| JP | 2010-201027 | A | 9/2010 |
| JP | 2011-206171 | A | 10/2011 |
| JP | 2012-223426 | A | 11/2012 |
| WO | 92/03178 | A1 | 3/1992 |
| WO | 93/20882 | A1 | 10/1993 |
| WO | 96/20752 | A1 | 7/1996 |

OTHER PUBLICATIONS

International Search Report (PCT/ISA/210) dated May 7, 2013, by the Japanese Patent Office as the International Searching Authority for International Application No. PCT/JP2013/052925.
European Search Report dated Sep. 9, 2016, by the European Patent Office, in corresponding European Patent Application No. 13874342.2 (6 pages).
Japanese Official Action dated Nov. 8, 2016, by the Japan Patent Office, in corresponding Japanese Patent Application No. 2014-560599 (4 pages).
Office Action (First Official Action) dated Apr. 24, 2017, by the State Intellectual Property Office of People's Republic of China in corresponding Chinese Patent Application No. 201380072583.2. (7 pages).

* cited by examiner

US 10,058,677 B2

BALLOON CATHETER

TECHNICAL FIELD

The present invention relates to a balloon catheter and more particularly to a balloon catheter to be inserted into a blood vessel to occlude the blood vessel.

BACKGROUND ART

The balloon catheter is used to perform angiography, inject a liquid medicine such as a chemotherapeutic agent into a blood vessel, and vascular embolization.

A balloon catheter was proposed as disclosed in a patent document 1 (Japanese Patent Application Laid-Open Publication No. 2005-103120) by the applicant of this application.

The balloon catheter 1 of the patent document 1 has the double tube-structured catheter main body 3 having the inner tube 9 and the outer tube 21. The balloon 3 is mounted on the catheter main body at its front end portion. The injection liquid passage 23 formed between the inner tube and the outer tube communicates with the inside of the catheter main body through the opening 22 formed at the front end of the outer tube.

A catheter provided with an expandable body is disclosed in a patent document 2 (Japanese Patent Application Laid-Open Publication No. H09-10314). In the catheter with the expandable body, the outer tube 1 and the inner tube 2 are coaxially disposed. The outer tube 1 is constructed of the flexible front end part 11, the intermediate part 12 whose inner and outer diameters are larger than those of the front end part 11, and the thick proximal end part 13 whose inner and outer diameters are larger than those of the intermediate part 12. The outer tube has the contractible and foldable expandable body 10 at the front end part 11 thereof. The catheter is smoothly, integrally, and seamlessly formed from the front end part 11 including the expandable body 10 to the proximal end part 13.

PRIOR ART DOCUMENTS

Patent Documents

Patent document 1: Japanese Patent Application Laid-Open Publication No. 2005-103120
Patent document 2: Japanese Patent Application Laid-Open Publication No. H09-10314

SUMMARY OF THE INVENTION

Problems to be Solved by the Invention

Recently balloon catheters as disclosed in the patent document 1 are demanded that the balloon catheters are thin and can be inserted into a curved blood vessel.

The expandable body-provided catheter of the patent document 2 is smoothly, integrally, and seamlessly formed from the front end part 11 including the expandable body 10 to the proximal end part 13 and does not have change points at which the properties of the materials used for the catheter change abruptly. The contractible and foldable expandable body is used. But the catheter of the patent document 2 is used to expand a narrow pass generated in a blood vessel and increase the flow rate of blood at the distal side of the narrow pass. To do so, the expandable body is expanded by injecting a liquid thereinto at a high pressure.

The balloon catheter to be used for blood vessel embolization is demanded to securely occlude a blood vessel at a low injection pressure by utilizing elastic deformation of the balloon because the blood vessel into which the balloon catheter is inserted has a small diameter and the inner wall of the blood vessel should be prevented from being damaged.

Therefore, it is an object of the present invention to provide a balloon catheter which can be inserted into a curved blood vessel having a small diameter and which allows a balloon to be securely expanded by a low liquid pressure to thereby securely occlude the blood vessel.

Means for Solving the Problems

The means for achieving the above-described object is as described below.

A balloon catheter has an inner tube having a first lumen, an outer tube part provided coaxially with the inner tube and forming a second lumen between the outer tube part and an outer surface of the inner tube, and a balloon part, a front end portion of which is fixed to a front end portion of the inner tube and an inside of which communicates with the second lumen. The balloon part has a bulged portion, having an expansion forming mode formed in advance, which is elastically deformable beyond the expansion forming mode by a balloon expansion liquid injected thereinto. The outer tube part has a front side sleeve portion which is extended from a rear end portion of the bulged portion of the balloon part toward a proximal end of the outer tube part, is formed integrally with the balloon part by using the same material as that to be used for the balloon part, and is substantially non-expandable.

MODE FOR CARRYING OUT THE INVENTION

Figure 1:
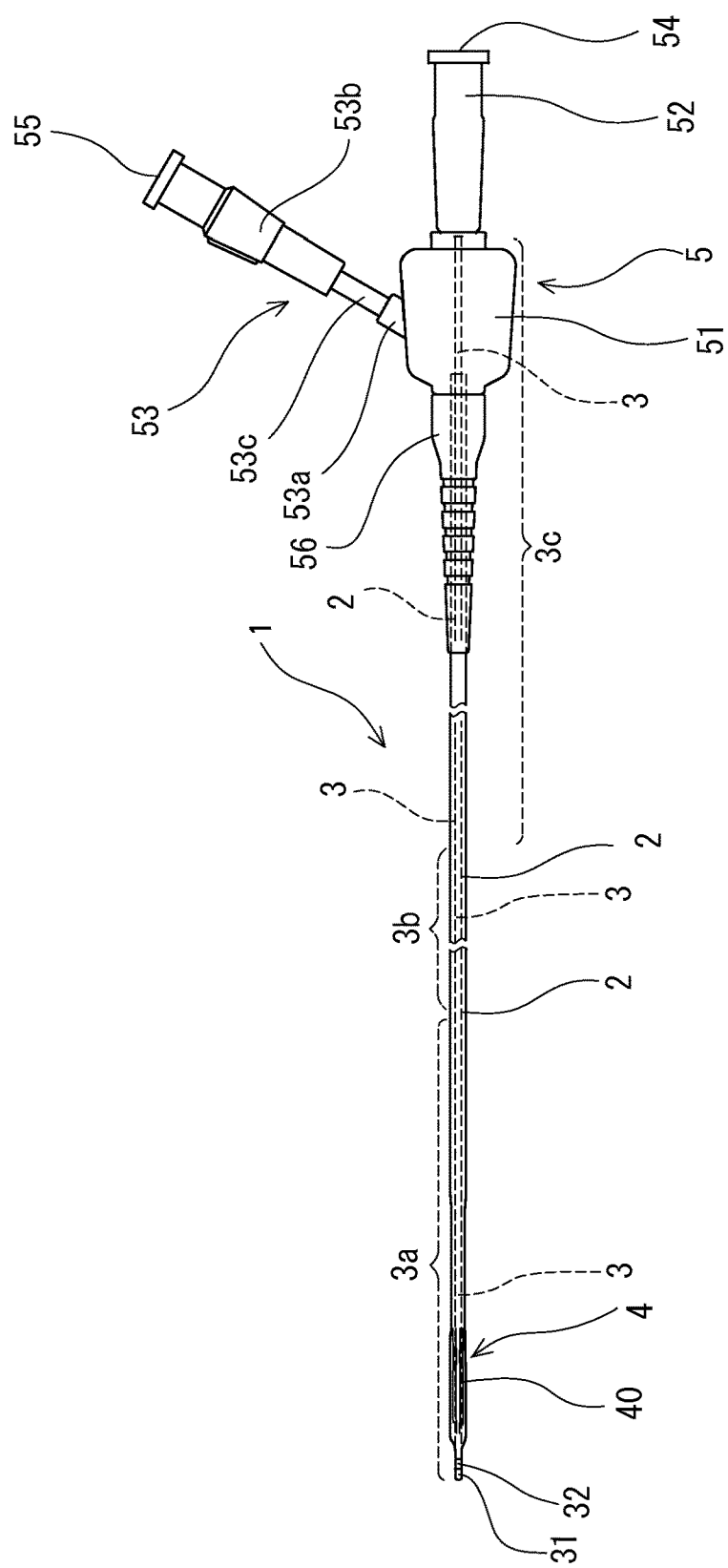
FIG. 1 is a partly abbreviated outside view of one embodiment of a balloon catheter of the present invention.

The balloon catheter of the present invention is described below by using embodiments shown in the drawings.

A balloon catheter 1 of the present invention has an inner tube 3 having a first lumen 11, an outer tube part 2 provided coaxially with the inner tube 3 and forming a second lumen between the outer tube part and an outer surface of the inner tube, and a balloon part 4, a front end portion of which is fixed to a front end portion of the inner tube 3 and an inner portion of which communicates with the second lumen 12. The balloon part 4 has a bulged portion 40, having an expansion forming mode formed in advance, which is elastically deformable beyond the expansion forming mode by a balloon expansion liquid injected thereinto. The outer tube part 2 has a front side sleeve portion 21 which is extended from a rear end portion of the bulged portion 40 of the balloon part 4 to a proximal end of the outer tube part, is formed integrally with the balloon part 4 by using the same material as that to be used for the balloon part 4, and is substantially non-expandable.

In balloon catheters 1, 10, and 20 shown in FIGS. 1 through 7, each of the outer tube parts 2 thereof is entirely formed integrally with the balloon part 4 by using the same material as that to be as used for the balloon part 4. In balloon catheters 100, 110, 130, 150, 160, and 170 shown in FIGS. 9 through 22, each of the outer tube parts thereof is constructed of a front side sleeve portion 120 and an outer tube main body 102, a front end portion of which is fixed to a rear end portion of the front side sleeve portion 120.

The balloon catheter of an embodiment shown in FIGS. 1 through 7 is described below.

The balloon catheter 1 of this embodiment is formed of the outer tube part 2 having the front side sleeve portion 21 integral with the balloon part 4, the inner tube 3, and a branch hub 5.

The inner tube 3 is a tubular body having the first lumen 11, a front end of which is open. The first lumen 11 is used to insert a guide wire into the inner tube and inject a liquid medicine and the like thereinto. In the balloon catheter 1 of this embodiment, the first lumen 11 of the inner tube 3 communicates with a first open portion 54 provided on the branch hub 5.

It is favorable to set the outer diameter of the inner tube 3 to 0.6 to 1.7 mm and especially favorable to set the outer diameter thereof to 0.6 to 0.7 mm. It is favorable to set the inner diameter of the inner tube to 0.4 to 1.4 mm and especially favorable to set the inner diameter thereof to 0.4 to 0.50 mm.

The inner tube 3 is inserted into the outer tube part 2 in such a way that a front end portion thereof is projected forward beyond the outer tube part 2. The second lumen 12 (balloon-expanding lumen) is formed between the outer surface of the inner tube 3 and an inner surface of the outer tube part 2 and has a sufficiently large volume.

Figure 3:
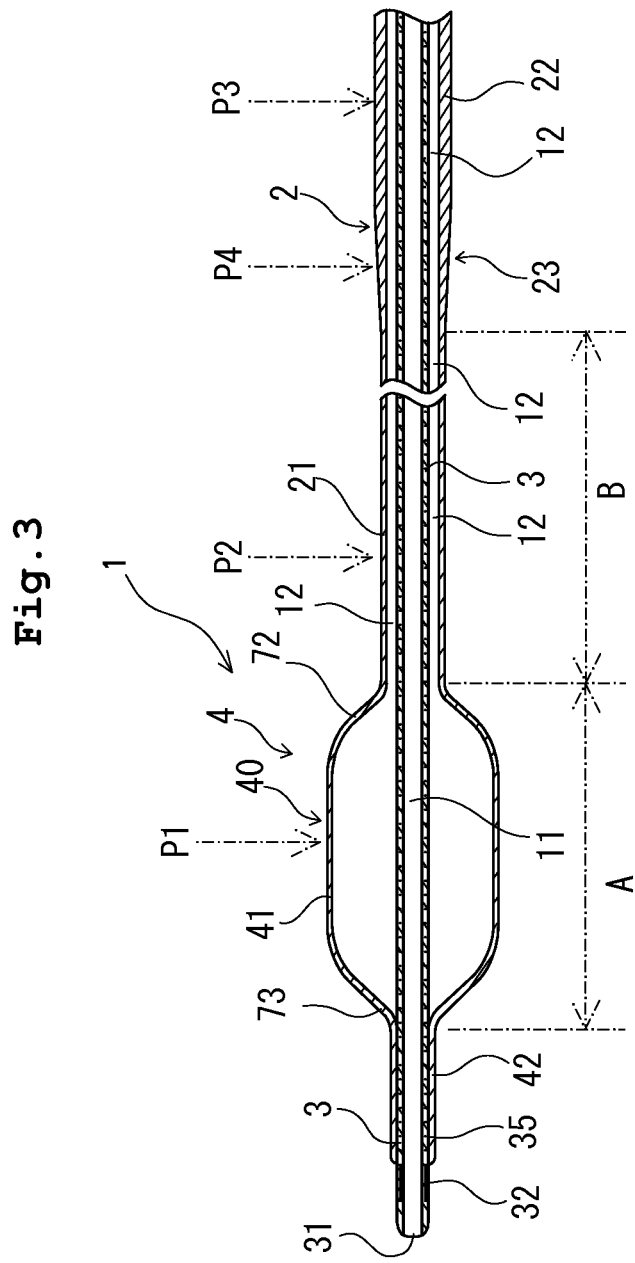
FIG. 3 is an enlarged vertical sectional view of the front end portion of the balloon catheter shown in FIG. 1 when a balloon expands.

An imaging marker 32 is fixed to the inner tube 3 at its front end portion (disposed a little proximal from a front end 31 of the inner tube and in the neighborhood of a front end portion 42 of the balloon part 4). It is preferable to form the imaging marker of a radiopaque material (for example, gold, platinum, tungsten or alloys of these metals or a silver-palladium alloy, a platinum-iridium alloy). By so doing, it is possible to check the front end portion of the balloon catheter 1 by means of radiographic visualization. The inner tube 3 may be provided with a rigidity-imparting body 35. As the rigidity-imparting body, a blade formed of a metal wire or a synthetic resin wire is preferable. In the case where the inner tube 3 is provided with the rigidity-imparting body, it is preferable to provide the rigidity-imparting body entirely on the inner tube except for the front end portion thereof, as shown in FIG. 3. More specifically, it is preferable to provide the rigidity-imparting body on the inner tube in a range from the imaging marker 32 to the proximal end thereof.

In the balloon catheter of this embodiment, as shown in FIG. 1, the inner tube 3 has a first flexible region 3a disposed at a front side of the inner tube 3, a second flexible region 3b which is continuous with the first flexible region 3a and flexible but has a higher hardness than the first flexible region 3a, and a flexible region 3c which is continuous with the second flexible region 3b and has a higher hardness than the second flexible region 3b. In this embodiment, as shown in FIG. 1, the most flexible first flexible region 3a is extended rearward from the front end of the inner tube 3. A rear end of the first flexible region 3a is positioned rearward from the front thereof by a predetermined length. The length of the first flexible region 3a is set to favorably 100 to 350 mm and especially favorably 200 to 300 mm.

It is preferable to set a three-point bending load value of the first region 3a per unit deflection to 20 to 75 mN/mm. The length of the second flexible region 3b continuous with the first flexible region 3a is set to favorably 100 to 350 mm and especially favorably 200 to 300 mm. It is preferable to set a three-point bending load value of the second region 3b per unit deflection to 65 to 105 mN/mm. It is preferable to set the three-point bending load value of the second region 3b per unit deflection higher than that of the first flexible region by 10 to 85 mN/mm. The length of the third flexible region 3c continuous with the second flexible region 3b is set to favorably 500 to 1500 mm and especially favorably 800 to 1200 mm. It is preferable to set the three-point bending load value of the third region 3c per unit deflection to 95 to 320 mN/mm. It is preferable to set the three-point bending load value of the third region 3c per unit deflection higher than that of the second flexible region 3b by 30 to 250 mm.

A portion of the inner tube 3 in the vicinity of a portion thereof to be fixed to the outer tube may be formed as an easily deformable portion more deformable than other portions of the inner tube. The easily deformable portion can be formed by not forming the rigidity-imparting body on only the portion of the inner tube in the vicinity of the portion thereof to be fixed to the outer tube or by thinning only the portion of the inner tube in the vicinity of the portion thereof to be fixed to the outer tube.

As materials to be used to form the inner tube 3, materials having hardness and flexibility to some extent are preferable. It is possible to use polyolefin such as polyolefin and polypropylene; polyester such as polyamide an polyethylene terephthalate; fluorine-based polymer such as PTFE and ETFE; PEEK (polyether ether ketone); polyimide; synthetic resin elastomer such as olefinic elastomer (for example, polyethylene elastomer and polypropylene elastomer), polyamide elastomer, styrenic elastomer (for example, a styrene-butadiene-styrene copolymer, a styrene-isoprene-styrene copolymer, a styrene-ethylene butylene-styrene copolymer); polyurethane, urethane-based elastomer, and fluorine-based elastomer; synthetic rubber such as urethane rubber, silicone rubber, and butadiene rubber; and natural rubbers such as latex rubber.

Figure 8:
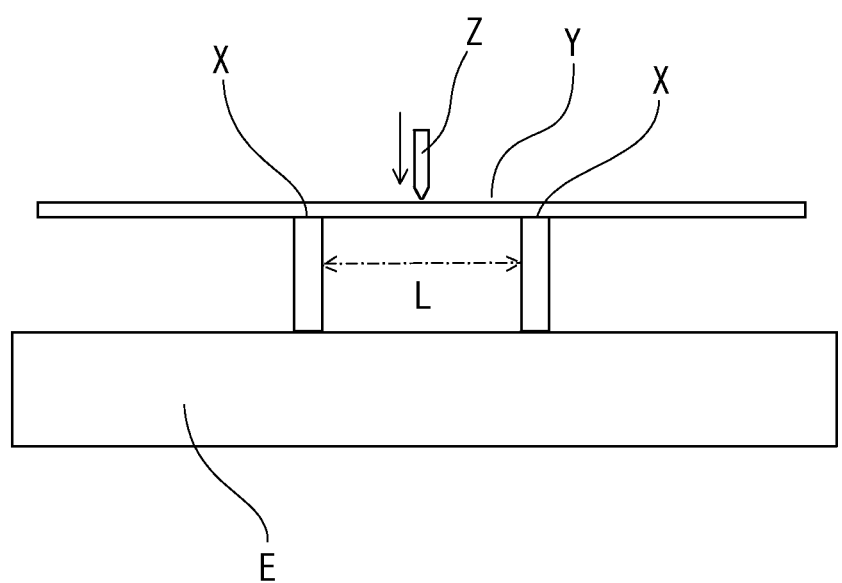
FIG. 8 is an explanatory view for explaining a method of the present invention for measuring a three-point bending load value per unit deflection.

In the present invention, as shown in FIG. 8, the three-point bending load value per unit deflection means a load value measured when a load is applied to the center of a test sample Y supported on a supporting table E between supporting points X-X spaced at a certain distance (L) by vertically moving a pressurizing metal rod Z (outer diameter: 1.5 mm) by a certain distance. In the present invention, the distance between supporting points was set to 10 mm. The testing apparatus used was RTC-1210A (produced by Orientech Co., Ltd.). The vertical movement distance of the pressurizing rod was 2.0 mm. The test speed of the pressurizing rod was 5.0 mm/minute. Load values when the test sample was pressed by the pressurizing rod by 1.0 mm were recorded. In the present invention, the three-point bending load value per unit deflection is used as an index to simply indicate the rigidity of the catheter.

The outer tube part 2 is a tubular body into which the inner tube 3 is inserted to such an extent that a front end portion (proximal portion of balloon) of the outer tube part is positioned at a portion (proximal from the front end of the inner tube by a predetermined length) rearward from the front end of the inner tube 3 by a predetermined length. A front end of the second lumen 12 communicates with a rear end of a front side sleeve portion 21 which is described later. A rear end of the second lumen 12 communicates with a second open portion 55 of an injection port 53, provided on the branch hub 5, into which a balloon-expanding fluid (for example, balloon-expanding liquid, specifically angiographic agent) is injected.

It is favorable to set the outer diameter of the outer tube part 2 to 0.8 to 2.0 mm and especially favorable to set the outer diameter thereof to 0.8 to 1.0 mm. It is favorable to set the inner diameter of the outer tube part to 0.7 to 1.9 mm and especially favorable to set the inner diameter thereof to 0.7 to 0.8 mm.

In the balloon catheter 1 of this embodiment, the outer tube part 2 has the front side sleeve portion 21 and an outer tube main body 22 which is extended from a rear end portion of the front side sleeve portion 21 to the proximal end of the balloon catheter 1 and is harder than the front side sleeve portion 21.

The outer tube main body 22 of the outer tube part 2 may be provided with the rigidity-imparting body. As the rigidity-imparting body, the blade formed of the metal wire or the synthetic resin wire is preferable.

In the balloon catheter 1 of this embodiment, a three-point bending load value A1 per unit deflection at an expandable portion P1 of the balloon part 4, a three-point bending load value A2 per unit deflection at the front side sleeve portion 21 (P2), and a three-point bending load value A3 per unit deflection at a front side portion P3 of the outer tube main body 22 are set to A1<A2<A3. The difference between the three-point bending load value A1 and the three-point bending load value A3 is set to not more than 300 mN/mm. The three-point bending load value A1 is set to not more than 50 mN/mm.

The three-point bending load value A1 is measured at an expandable portion 41 of the balloon part 4 at which the inner tube 3 does not have the marker. In the case where the marker is not provided at a central portion of the expandable portion 41, it is preferable to measure the three-point bending load value A1 at the central portion of the expandable portion.

It is preferable to set the three-point bending load value A1 and a three-point bending load value A4 per unit deflection at a boundary portion 23 (P4) between the front side sleeve portion 21 and the outer tube main body 22 to A1<A4, the difference between the three-point bending load value A1 and the three-point bending load value A4 to not more than 50 mN/mm, the three-point bending load value A1 to not more than 50 mN/mm. Therefore, it is especially preferable to set the three-point bending load values A1, A2, A3, and A4 to A1<A2<A4<A3.

Therefore, the flexibility of the balloon of the catheter becomes stepwise lower from its front end to its rear end. In other words, the flexibility of the balloon becomes stepwise harder. Therefore, kink hardly occurs in the front side (flexibility change region) of the balloon. Further because there is little difference in the flexibility (hardness) at the front side (flexibility change region) of the balloon where there is a change in the flexibility, the balloon is capable of passing through a curved portion of a blood vessel to a high extent. Therefore, the balloon catheter of the present invention can be inserted into lumens with a high degree of operability.

It is preferable to set the three-point bending load value A1 of the balloon catheter 1 to not more than 40 mN/mm. It is preferable to set the three-point bending load value A2 to not more than 80 mN/mm. It is preferable to set the three-point bending load value A3 to not more than 350 mN/mm and especially preferable to set it to not more than 130 mN/mm. It is preferable to set the three-point bending load value A4 to not more than 120 mN/mm and especially preferable to set it to not more than 100 mN/mm. It is also preferable to set a three-point bending load value A5 per unit deflection at a proximal portion of the outer tube main body 22 larger than the three-point bending load value A3 at a front end portion of the outer tube main body 22 and set the difference between the three-point bending load value A3 and the three-point bending load value A5 to not more than 450 mN/mm.

Figure 5:
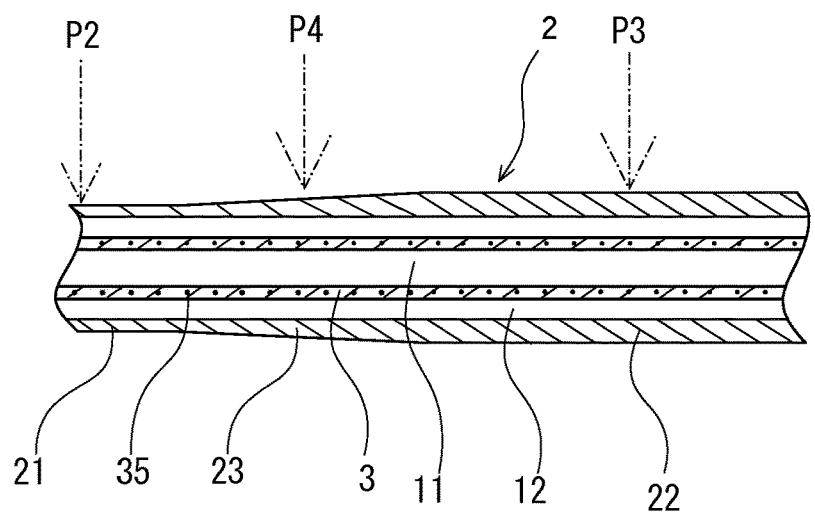
FIG. 5 is an explanatory view for explaining the balloon catheter of the present invention.
Figure 6:
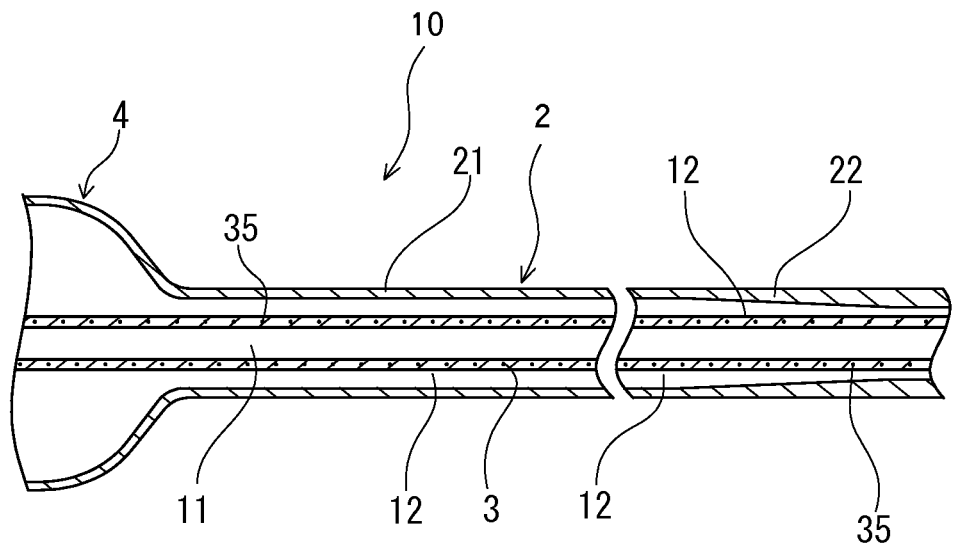
FIG. 6 is an explanatory view for explaining a balloon catheter of another embodiment of the present invention.
Figure 7:
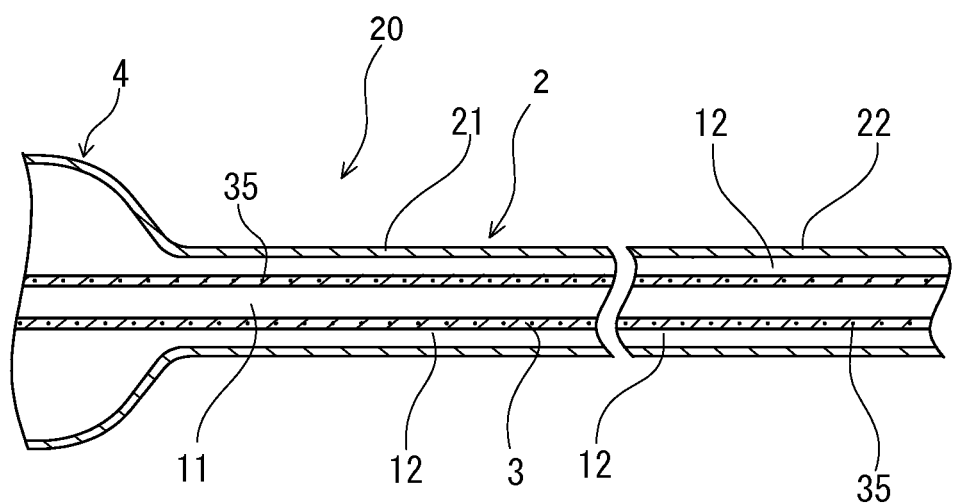
FIG. 7 is an explanatory view for explaining a balloon catheter of another embodiment of the present invention.

As shown in FIG. 5, the boundary portion 23 disposed between the front side sleeve portion 21 of the outer tube part 2 and the outer tube main body 22 thereof has a tilt property that the hardness gradually becomes higher from the proximal end of the front side sleeve portion 21 to the front end of the outer tube main body 22. More specifically, the boundary portion 23 becomes gradually thicker from the proximal end of the front side sleeve portion 21 to the front end of the outer tube main body 22 with the inner diameter of the boundary portion being substantially unchanged and the outer diameter thereof becoming gradually thicker. The balloon catheter of the present invention is not limited to the above-described mode, but like a balloon catheter 10 of an embodiment shown in FIG. 6, it is possible to form the boundary portion 23 which becomes gradually thicker from the proximal end of the front side sleeve portion 21 to the front end of the outer tube main body 22 with the inner diameter of the boundary portion becoming gradually smaller and the outer diameter thereof being substantially unchanged. In addition, although it is preferable to provide the balloon catheter with the boundary portion, like a balloon catheter 20 of an embodiment shown in FIG. 7, it is possible to form a balloon catheter, not having the boundary portion, in which the entire outer tube part 2 has almost the same property. In this embodiment, the front side sleeve portion 21 and the outer tube main body 22 have the same property.

The balloon part 4 has the expansion forming mode formed in advance and can be expanded by the balloon-expanding liquid injected thereinto. More specifically, the balloon part 4 has the bulged portion 40 having the expansion forming mode formed by plastic deformation and a front side tubular portion 42, formed at a front side of the bulged portion 40, which is smaller than the bulged portion 40 in its diameter and thicker than the bulged portion 40 and substantially non-expandable. The front side sleeve portion 21 which is smaller than the bulged portion 40 in its diameter and thicker than the bulged portion 40 and substantially non-expandable is disposed at a rear side of the bulged portion 40. The bulged portion 40 has an elastically deformable portion 41. The elastically deformable portion 41 can be extended owing to elastic deformation caused by an internal pressure applied thereto. In the catheter of this embodiment, it is preferable to configure the balloon part 4 into a diameter-decreased mode having wrinkles 71 extending axially. The bulged portion 40 is so formed that it does not have wrinkles extending circumferentially.

The bulged portion 40 of the balloon part 4 is expanded by the liquid injected thereinto and elastically deforms beyond the formation mode, thus being capable of closely contacting the inner wall of a blood vessel. More specifically, the bulged portion 40 is restored to a molded mode from the diameter-decreased mode and is thereafter extendable (expandable). Thereby, the bulged portion securely closely contacts the inner wall of the blood vessel and does not damage the inner wall. In this embodiment, the bulged portion 40 is formed by stretching at temperatures not less than its glass transition point and less than its softening point. The bulged portion 40 expands without being subjected to resistance until before the mode of the plastic deformation (molded mode) thereof finishes. Thereafter the bulged portion is expanded (extended) by the elastic deformation according to the pressure of the balloon-expanding liquid injected thereinto. Thereafter owing to a decrease in the pressure, the bulged portion is restored to the mode before the bulged portion is expanded by the elastic deformation.

In the balloon catheter 1 of this embodiment, the balloon part 4 has the bulged portion 40 formed in the expansion forming mode by the plastic deformation. The bulged portion 40 has the elastically deformable portion 41, a front side tapered portion 73, provided forward from the elastically deformable portion 41, which decreases toward its front end in its diameter and is substantially elastically undeformable, and a rear side tapered portion 72, provided rearward from the elastically deformable portion, which decreases toward its rear end in its diameter and is substantially elastically undeformable. The elastically deformable portion 41 is expandable in its diameter to such an extent that its diameter becomes larger than its diameter obtained when the elastically deformable portion is formed by molding the material. More specifically, it is favorable that without breakage, the elastically deformable portion is expandable by not less than 2 R as compared with its outer diameter R the elastically deformable portion has in the formation mode. It is more favorable that without breakage, the elastically deformable portion 41 is expandable by not less than 2.5 R as compared with its outer diameter R it has in the formation mode.

The thickness of the bulged portion 40 is smaller than that of the front side tubular portion 42 and that of the front side sleeve portion 21. The front side tubular portion 42 and the front side sleeve portion 21 are not substantially radially stretched. The bulged portion 40 has the elastically deformable portion 41, the front side tapered portion 73, and the rear side tapered portion 72. The front side tapered portion 73 and the rear side tapered portion 72 are formed as thickness change portions which become gradually thinner toward the elastically deformable portion 41. The front side tapered portion 73 and the rear side tapered portion 72 are substantially elastically undeformable.

As described later, it is preferable to form the bulged portion 40 owing to the plastic deformation caused by the internal pressure partly applied to the synthetic resin which is the material for the bulged portion at temperatures not less than the glass transition point of the synthetic resin and not more than the softening point thereof. It is preferable to configure the bulged portion 40 into the diameter-decreased state in which the diameter thereof is made smaller than that of the plastic deformation mode of the bulged portion formed by the plastic deformation. It is preferable to configure the bulged portion into the diameter-decreased state by heat-setting. The heat-setting is carried out by heating and by pressurizing used a heat-shrinkable tube. By so doing, it is possible to securely configure the bulged portion into the diameter-decreased mode having the wrinkles 71 extending axially.

It is preferable to heat-set the heat-shrinkable tube at a temperature in the neighborhood of the softening point of the synthetic resin or a temperature lower than the softening point thereof by not more than 10 degrees. By so doing, it is possible to securely configure the bulged portion into the diameter-decreased mode having the wrinkles 71 extending axially without adversely affecting the plastic deformation of the bulged portion.

The front side tubular portion 42 is a short tubular portion extending in almost an equal outer diameter and having a larger thickness than the bulged portion 40. The front side sleeve portion 21 extends in almost an equal outer diameter and has a larger thickness than the bulged portion 40. The front side tubular portion 42 has a smaller outer diameter than the front side sleeve portion 21 and is fixed to the front end portion of the inner tube 3. It is preferable to dispose the forefront of the front side tubular portion 42 at a rear end of the imaging marker 32 or at a position proximate to the rear end of the imaging marker. It is preferable that the front side tubular portion 42 does not coat the imaging marker 32. It is preferable to fix the front side tubular portion 42 to the inner tube 3 by means of heat sealing.

The front side sleeve portion 21 does not substantially expand when the liquid is injected thereinto. The front side sleeve portion 21 forms a part of the balloon-expanding lumen 12 between the inner surface thereof and the outer surface of the inner tube 3.

As materials to be used to form the outer tube part 2 having the balloon part 4 integral therewith, thermoplastic synthetic resin which is elastically deformable when the thickness thereof is not more than a predetermined thickness, is elastically undeformable when the thickness thereof is not less than the predetermined thickness, and is flexible is used. More specifically, polyurethane elastomer and urethane elastomer, olefin elastomer (for example, polyethylene elastomer, polypropylene elastomer), polyester such as polyethylene terephthalate, soft polyvinyl chloride, polyamide elastomer and amide elastomer (for example, polyamide elastomer), fluororesin elastomer, and synthetic resin elastomer such as an ethylene-vinyl acetate copolymer are preferable. Thermoplastic polyurethane elastomer (for example, thermoplastic aromatic polyurethane elastomer, thermoplastic aliphatic polyurethane elastomer) is especially preferable. Examples of the thermoplastic polyurethane elastomer include thermoplastic aromatic and aliphatic polyurethane elastomers. As materials to be used to form the outer tube part 2 having the balloon part 4 integral therewith, it is possible to use synthetic rubber such as urethane rubber, silicone rubber, and butadiene rubber; and natural rubbers such as latex rubber.

As materials to be used to form the outer tube part 2 having the balloon part 4 integral therewith, materials having a glass transition point not more than 0 degree C. are favorable and those having the glass transition point not more than −10 degree C. are especially favorable. Materials having a softening point (Vicat softening point) not less than 70 degree C. are also favorable and those having the softening point in a range from 80 degree C. to 130 degree C. are especially favorable. The balloon part 4 has higher flexibility than the inner tube 3.

In the balloon part 4, the outer diameter (outer diameter when the bulged portion is restored to molded mode) of the bulged portion 40 is set to favorably 0.9 to 2.1 mm and especially favorably 0.9 to 1.0 mm. The outer diameter (expandable outer diameter) of the bulged portion is set to favorably 3.0 to 15.0 mm and especially favorably 4.0 to 8.0 mm when the bulged portion expands. The length of the bulged portion 40 is set to favorably 3.5 to 14.5 mm and especially favorably 4.0 to 5.5 mm. The radial stretch degree of the bulged portion is set to preferably 300 to 900. The axial stretch degree of the bulged portion is set to preferably 200 to 350%.

The outer diameter of the front side tubular portion 42 is set to favorably 0.6 to 1.9 mm and especially favorably 0.7 to 0.9 mm. The length of the front side tubular portion is set to favorably 1.0 to 3.0 mm and especially favorably 1.5 to 2.5 mm. The outer diameter of the front side sleeve portion 21 is set to favorably 0.9 to 2.1 mm and especially favorably 0.9 to 1.0 mm.

It is preferable to set the length B of the front side sleeve portion 21 to not less than 2.5 times as long as the length A of the expandable portion 41 of the balloon. It is especially preferable to set the length B of the front side sleeve portion 21 to not less than three times and less than six times as long as the length A of the expandable portion 41. It is favorable to set the length B of the front side sleeve portion 21 to 10 to 60 mm. It is more favorable to set the length B thereof to 15 to 45 mm and most favorable to set the length B thereof 20 to 30 mm. The length A of the expandable portion 41 includes the length of the front side tapered portion 73 and that of the rear side tapered portion 72.

The bulged portion 40 of the balloon part 4 is thinner than the front side tubular portion 42 and the front side sleeve portion 21. It is favorable to set the thickness of the bulged portion 40 smaller than that of the front side sleeve portion 21 and that of the front side tubular portion 42 by 0.03 to 0.18 mm and especially favorable to set the thickness thereof smaller than that of the front side sleeve portion and that the front side tubular portion by 0.04 to 0.11 mm. It is favorable to set the thickness of the front side sleeve portion 21 and that of the front side tubular portion 42 to 0.07 to 0.20 mm and especially favorable to set the thickness thereof to 0.08 to 0.15 mm.

Figure 2:
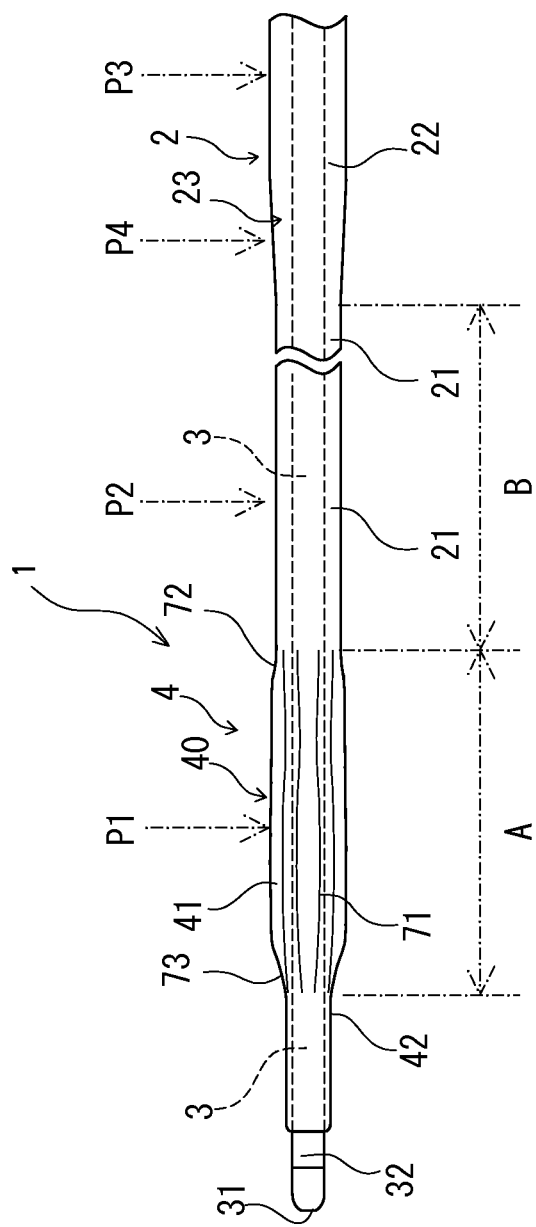
FIG. 2 is an enlarged outside view of a front end portion of the balloon catheter shown in FIG. 1.

In the catheter 1 of this embodiment, the balloon part 4 is fixed to the inner tube with the balloon part 4 being axially stretched. Therefore, as shown in FIG. 2, the balloon part 4 is a little axially stretched. Thus there is a further decrease in the diameter of the bulged portion configured in the diameter-decreased mode.

It is favorable that the balloon catheter of the present invention can be inserted into a guiding catheter having an inner diameter of 1.1 mm and especially favorable that it can be inserted into the guiding catheter having an inner diameter of 0.95 mm. By forming the catheter having such a small diameter, it is possible to insert the catheter into lumens (into blood vessels) having a small diameter. It is preferable that in the balloon catheter of the present invention, a guide wire having an outer diameter of 0.36 mm can be inserted into the inner tube and it is preferable that a guide wire having an outer diameter of 0.53 mm can be inserted into the inner tube. By setting the inner diameter of the inner tube to such an extent, it is possible to use the guide wire which has a thickness to some extent and is capable of displaying a sufficient guide function and easy to insert the catheter into lumens (into blood vessels).

Figure 4:
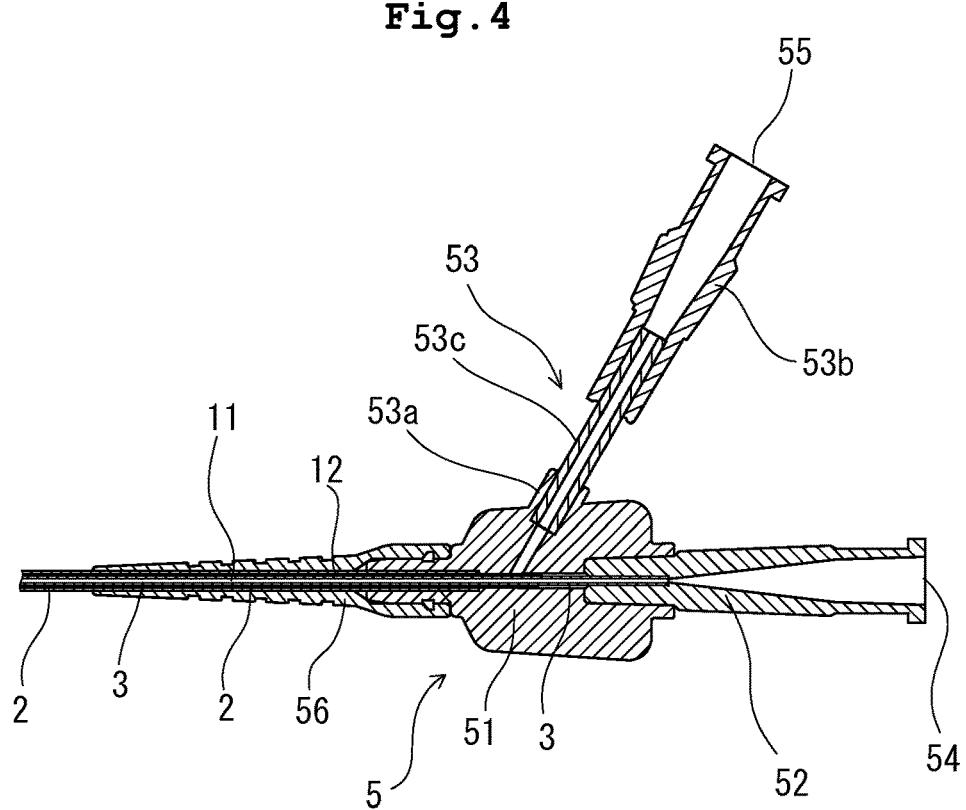
FIG. 4 is an enlarged vertical sectional view of a proximal part of the balloon catheter shown in FIG. 1.

As shown in FIG. 4, the branch hub 5 has an inner tube hub 52 which has the first open portion 54 communicating with the first lumen 11 and is fixed to the rear end portion of the inner tube 3 and an outer tube hub 51 which has the second open portion 55 communicating with the second lumen 12 and forming the injection port 53 and is fixed to the rear end portion of the outer tube part 2. The outer tube hub 51 and the inner tube hub 52 are fixed to each other. The outer tube hub 51 and the inner tube hub 52 are fixed to each other by inserting the inner tube 3 into a rear end of the outer tube hub 51 mounted on the proximal portion of the outer tube part 2 from the front end of the inner tube 3 and joining. The branch hub 5 is provided with a bending prevention tube 56 covering the proximal portion of the outer tube part 2 and a front end portion of the branch hub 5. The injection port 53 is formed of a branch port 53*a* extended from a side wall of the outer tube hub 51, an injection port hub 53*b*, and a connection tube 53*c* connecting the branch port 53*a* and the injection port hub 53*b* to each other. As materials to be used to form the branch hub, it is possible to suitably use thermoplastic resin such as polycarbonate, polyamide, polysulfone, polyarylate, and a methacrylate-butylene-styrene copolymer. As the connection tube, a flexible synthetic resin or a soft synthetic resin is used.

The balloon catheter of the present invention is described below by using embodiments shown in FIGS. 9 through 22. In balloon catheters 100, 110, 130, 150, 160, and 170 shown in FIGS. 9 through 22, an outer tube part is constructed of a front side sleeve portion 120 and an outer tube main body 102 whose front end portion is fixed to a rear end portion of the front side sleeve portion 120.

The balloon catheter 100 of this embodiment has an inner tube 103 having a first lumen 111, the outer tube part which is provided coaxially with the inner tube 103, which has its front end positioned rearward from the front end of the inner tube 103 by a predetermined length, and which forms a second lumen 112 between the outer tube part and an outer surface of the inner tube 103, and an expandable balloon part 104 whose front end portion 142 is fixed to the inner tube 103, whose rear end portion 144 is fixed to the outer tube part, and whose inside communicates with the second lumen 112.

The balloon part 104 has an expansion forming mode formed in advance and can be expanded by a balloon expansion liquid injected thereinto. More specifically, the balloon part 104 has a bulged portion 140 having the expansion forming mode in which the bulged portion is formed by plastic deformation and the front side tubular portion 142, formed at a front side of the bulged portion 140, which is smaller than the bulged portion 140 in its diameter and thicker than the bulged portion and substantially non-expandable. A rear side of the bulged portion 140 is the front side sleeve portion 120 of the substantially non-expandable outer tube part and the front side sleeve portion 120 is smaller in diameter than the bulged portion 140 and thicker than the bulged portion 140. The bulged portion 140 has an elastically deformable portion 141. The elastically deformable portion 141 can be extended owing to elastic deformation caused by the internal pressure applied to the bulged portion 140. In the catheter of this embodiment, it is preferable to configure the balloon part 104 into a diameter-decreased mode having wrinkles 171 extending axially.

In the balloon catheter 100, a three-point bending load value A10 of an expandable portion of the balloon per unit deflection and a three-point bending load value A20 of a fixed portion per unit deflection where the rear end portion of the front side sleeve portion and the front end portion of the outer tube main body are fixed to each other are set to A10<A20. The difference between the three-point bending load value A10 and the three-point bending load value A20 is set to not more than 50 mN/mm. The three-point bending load value A10 is set to not more than 50 mN/mm.

The three-point bending load value A10 is measured at the expandable portion 141 of the balloon part 104 where the inner tube 103 does not have a marker. In the case where the marker is not disposed at a central portion of the expandable portion 141, it is preferable to measure the three-point bending load value A10 at the central portion of the expandable portion.

In the present invention, the three-point bending load value per unit deflection is measured by using the above-described method.

The balloon catheter 100 of this embodiment is formed of the outer tube part, the inner tube 103, the bulged portion 140, and a branch hub 105.

The inner tube 103 is a tubular body having the first lumen 111 whose front end is open. The first lumen 111 is used to insert a guide wire thereinto and inject a liquid medicine and the like thereinto. In the balloon catheter 100 of this embodiment, the first lumen 111 of the inner tube 103 communicates with a first open portion 154 provided on the branch hub 105.

It is favorable to set the outer diameter of the inner tube 103 to 0.6 to 1.7 mm and especially favorable to set the outer diameter thereof to 0.6 to 0.7 mm. It is favorable to set the inner diameter of the inner tube to 0.4 to 1.4 mm and especially favorable to set the inner diameter thereof to 0.4 to 0.5 mm.

The inner tube 103 is inserted into the outer tube part in such a way that a front end portion of the inner tube is projected beyond the outer tube part. A second lumen 112 (balloon-expanding lumen) is formed between the outer surface of the inner tube 103 and the inner surface of the outer tube part and has a sufficiently large volume.

Figure 11:
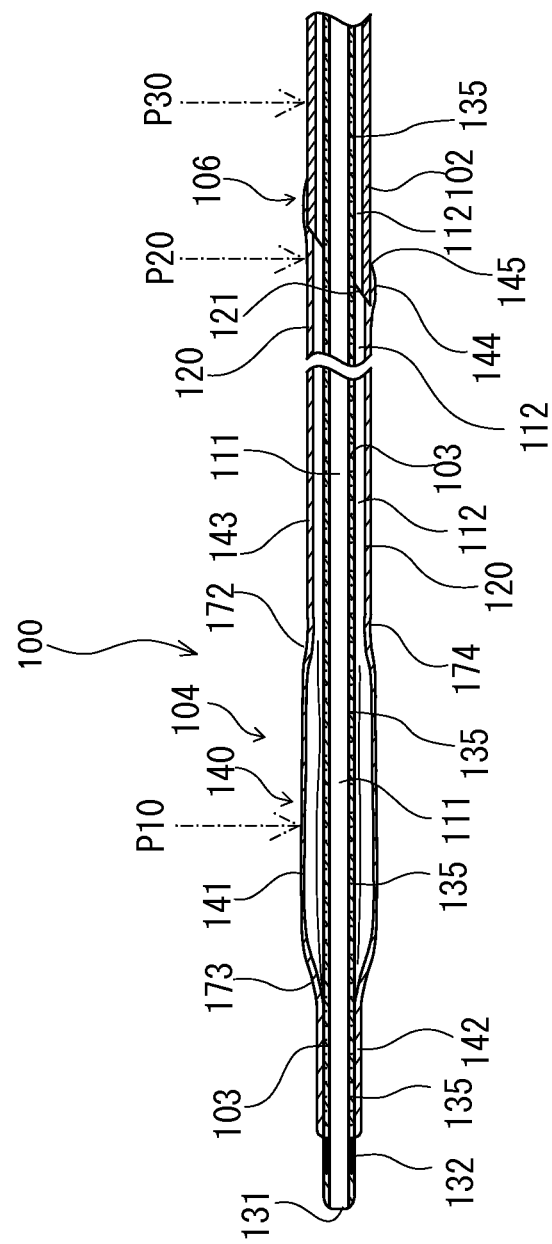
FIG. 11 is a vertical sectional view of FIG. 10.

An imaging marker 132 is fixed to the inner tube 103 at its front end portion (a little proximal from a front end 131 and in the neighborhood of a front end portion 142 of the balloon part 104). It is preferable to form the imaging marker of a radiopaque material (for example, gold, platinum, tungsten, alloys of these metals or a silver-palladium alloy, a platinum-iridium alloy). By so doing, it is possible to check a front end portion of the balloon catheter 100 by means of radiographic visualization. The inner tube 103 may be provided with a rigidity-imparting body 135. As the rigidity-imparting body, a blade formed of a metal wire or a synthetic resin wire is preferable. In the case where the inner tube 103 is provided with the rigidity-imparting body, it is preferable to dispose the rigidity-imparting body entirely on the inner tube except for its front end portion, as shown in FIG. 11. More specifically, it is preferable to dispose the rigidity-imparting body in a range from the imaging marker 132 to the proximal end of the inner tube.

Figure 9:
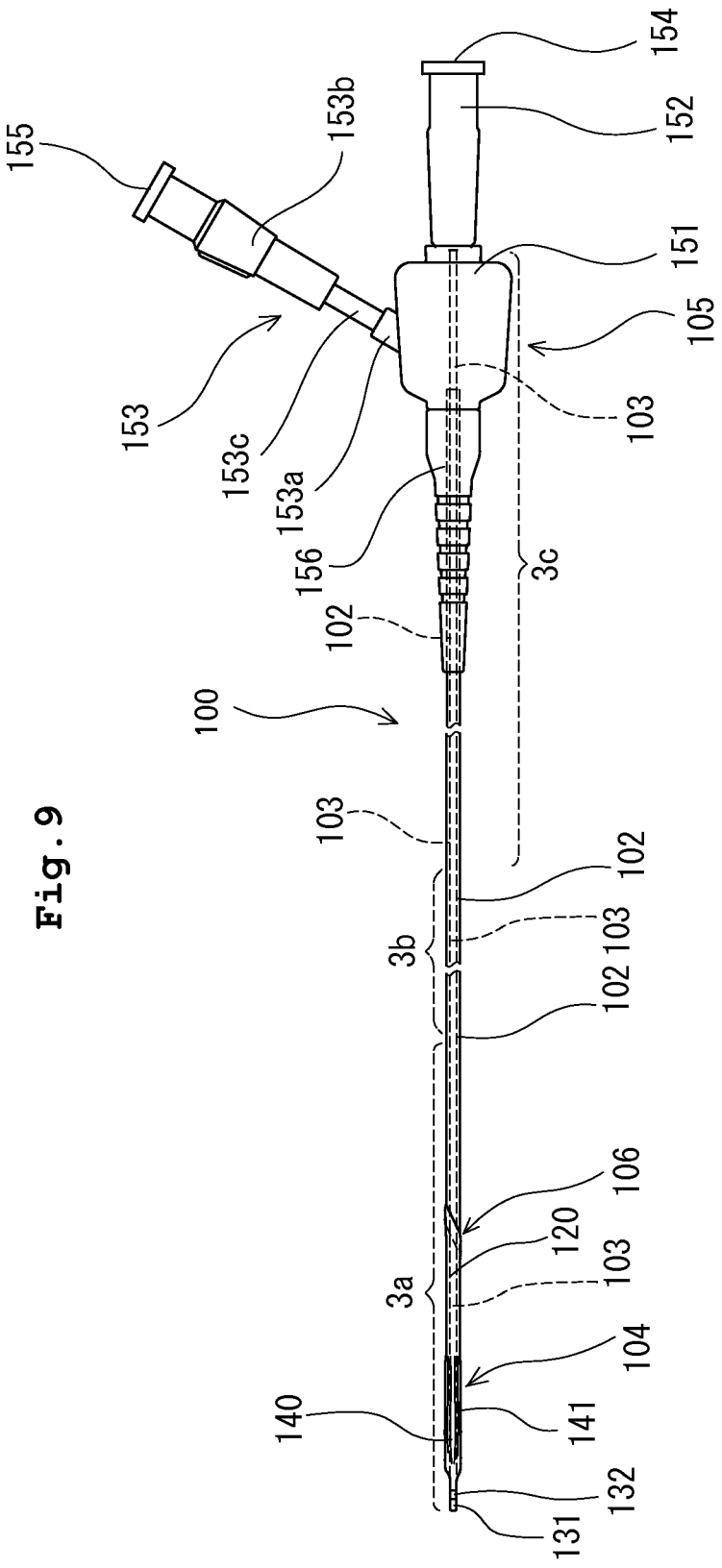
FIG. 9 is a partly abbreviated outside view of another embodiment of the balloon catheter of the present invention

In the balloon catheter of this embodiment, as shown in FIG. 9, the inner tube 103 has a first flexible region 3a disposed at the front side, a second flexible region 3b which is continuous with the first flexible region 3a and flexible, but has a higher hardness than the first flexible region 3a, and a flexible region 3c which is continuous with the second flexible region 3b and has a higher hardness than the second flexible region 3b. In this embodiment, as shown in FIG. 9, the most flexible first flexible region 3a is extended rearward from the front end of the inner tube 103 in such a way that a rear end of the first flexible region 3a passes beyond a belt-shaped tilted annular fixing portion 106 disposed between the outer tube main body 102 which is described later and the front side sleeve portion 120 and is positioned rearward from the belt-shaped tilted annular fixing portion by a predetermined length. The length of the first flexible region 3a is set to favorably 100 to 350 mm and especially favorably 200 to 300 mm.

It is preferable to set a three-point bending load value of the first region 3a per unit deflection to 20 to 75 mN/mm. The length of the second flexible region 3b continuous with the first flexible region 3a is set to favorably 100 to 350 mm and especially favorably 200 to 300 mm. It is preferable to set a three-point bending load value of the second region 3b per unit deflection to 65 to 105 mN/mm. It is preferable to set the three-point bending load value of the second region 3b per unit deflection higher than that of the first flexible region by 10 to 85 mN/mm. The length of the third flexible region 3c continuous with the second flexible region 3b is set to favorably 500 to 1500 mm and especially favorably 800 to 1200 mm. It is preferable to set the three-point bending load value of the third region 3c per unit deflection to 95 to 320 mN/mm. It is preferable to set the three-point bending load value of the third region 3c per unit deflection higher than that of the second flexible region 3b by 30 to 250 mm.

A portion of the inner tube 103 in the vicinity of a portion thereof fixed to the outer tube may be formed as an easily deformable portion more deformable than other portions of the inner tube. The easily deformable portion having the above-described mode can be formed by not forming the rigidity-imparting body on only the portion of the inner tube in the vicinity of the portion thereof fixed to the outer tube and by thinning only the portion of the inner tube in the vicinity of the portion thereof fixed to the outer tube.

The outer tube part is a tubular body into which the inner tube 103 is inserted. A rear end of the second lumen 112 communicates with a second open portion 155 of an injection port 153, provided on the branch hub 105, into which a balloon-expanding fluid (for example, balloon-expanding liquid, specifically angiographic agent) is injected.

The outer tube part is formed of the front side sleeve portion 120 and the outer tube main body 102.

It is favorable to set the outer diameter of the outer tube part to 0.8 to 2.0 mm and especially favorable to set the outer diameter thereof to 0.8 to 1.0 mm. It is favorable to set the inner diameter of the outer tube part to 0.7 to 1.9 mm and especially favorable to set the inner diameter thereof to 0.7 to 0.8 mm The front side sleeve portion 120 of the outer tube part does not substantially expand when the liquid is injected thereinto. The front side sleeve portion 21 forms a part of the balloon-expanding lumen 12 between the inner surface thereof and the outer surface of the inner tube 103. By composing the front side of the outer tube part of the front side sleeve portion 120 axially extended in a predetermined length, the front side of the outer tube part has higher flexibility than the outer tube main body 102. Thus the front side of the outer tube part is deformable, which allows low profiling (decrease of the outer diameter of the balloon catheter in inserting it into a living body) to be accomplished and the balloon catheter to be easily inserted into a lumen (for example, blood vessel) having a small diameter.

The outer diameter of the front side sleeve portion 120 is set to favorably 0.9 to 2.1 mm and especially favorably 0.9 to 1.0 mm. The length of the front side sleeve portion 120 is set to favorably 10 to 60 mm and especially favorably 15 to 30 mm.

It is preferable to form the front end portion of the outer tube main body 102 as an easily deformable front end portion more deformable than other portions of the outer tube main body. In this embodiment, the outer tube main body 102 has a tilted front end surface 121 which is oblique to the central axis of the outer tube main body 102 at the front end portion thereof. The front end of tilted front end surface 121 is soft. Like an embodiment shown in FIGS. 21 and 22, it is possible to allow the front end of the outer tube main body 102 to flexible by forming the front end portion of the outer tube main body 102 as the thin front end portion or by forming a slit at the front end portion thereof.

As materials to be used to form the outer tube main body 102 and the inner tube 103, materials having hardness and flexibility to some extent are preferable. It is possible to use polyolefin such as polyolefin and polypropylene; polyester such as polyamide an polyethylene terephthalate; fluorine-based polymer such as PTFE and ETFE; PEEK (polyether ether ketone); polyimide; synthetic resin elastomer such as olefinic elastomer (for example, polyethylene elastomer and polypropylene elastomer), polyamide elastomer, styrenic elastomer (for example, a styrene-butadiene-styrene copolymer, a styrene-isoprene-styrene copolymer, a styrene-ethylene butylene-styrene copolymer); polyurethane, urethane-based elastomer, and fluorine-based elastomer; synthetic rubber such as urethane rubber, silicone rubber, and butadiene rubber; and natural rubbers such as latex rubber.

The outer tube main body 102 may be provided with a rigidity-imparting body. As the rigidity-imparting body, a blade formed of a metal wire or a synthetic resin wire is preferable.

The expandable portion 141 of the balloon part 104 is expanded by a liquid injected thereinto and capable of closely contacting the inner wall of a blood vessel. More specifically, the expandable portion 141 is restored to a molded mode from a configured diameter-decreased mode by the balloon-expanding liquid injected thereinto and thereafter extendable (expandable). Thereby the expandable portion securely closely contacts the inner wall of the blood vessel and does not damage the inner wall. In this embodiment, the expandable portion 141 is formed by stretching a material at temperatures not less than its glass transition point and less than its softening point. The expandable portion expands without being subjected to resistance until before the mode of the plastic deformation (molded mode) thereof finishes. Thereafter the bulged portion is expanded (extended) by the elastic deformation according to the pressure of the balloon-expanding liquid injected thereinto. Thereafter owing to a decrease in the pressure, the bulged portion is restored to the mode before the bulged portion is expanded by the elastic deformation.

The thickness of the expandable portion 141 is smaller than that of front side tubular portion 142 and that of the front side sleeve portion 120 of the outer tube part. The front side tubular portion 142 and the front side sleeve portion 120 are not substantially radially stretched. A front side portion 173 of the expandable portion 141 and a rear side portion 172 thereof are formed as thickness change portions which become gradually thinner toward the expandable portion 41. It is preferable to configure the front side portion 173 of the expandable portion 141 and the rear side portion 172 thereof into a mode in which the front side portion and the rear side portion fall down toward an inner side of the expandable portion 141. By so doing, it is possible to prevent a raised portion of the expandable portion 141 from constituting an obstacle when the balloon catheter is progressing inside the blood vessel, when the balloon catheter is inserted into a guiding catheter, and when the balloon catheter is accommodated in a container. Thereby a catheter insertion operation can be favorably performed.

As described later, it is preferable to form the expandable portion 141 owing to the plastic deformation caused by the internal pressure partly applied to the synthetic resin which is the material used to form the expandable portion at temperatures not less than the glass transition point of the synthetic resin and not more than the softening point thereof. It is preferable to configure the expandable portion 141 into the diameter-decreased state in which the diameter thereof is made smaller than that of the expandable portion having the expansion forming mode formed by the plastic deformation. It is preferable to configure the expandable portion into the diameter-decreased state by heat-setting. The heat-setting is carried out by heating and by pressurizing used a heat-shrinkable tube. By so doing, it is possible to securely configure the expandable portion 141 into the diameter-decreased mode having the wrinkles 171 extending axially.

It is preferable to heat-set the heat-shrinkable tube at a temperature in the neighborhood of the softening point of the synthetic resin or a temperature lower than the softening point thereof by not more than 10 degrees. By so doing, it is possible to securely configure the expandable portion into the diameter-decreased mode having the wrinkles extending axially without adversely affecting the plastic deformation of the expandable portion.

The front side tubular portion 142 is a short tubular portion extending in almost an equal outer diameter and having a larger thickness than the expandable portion 141. The front side sleeve portion 120 of the outer tube part extends in almost an equal outer diameter and is axially longer than the front side tubular portion 142 and is thicker than the expandable portion 141. The front side tubular portion 142 has a smaller outer diameter than the front side sleeve portion 120 and is fixed to the front end portion of the inner tube 103. It is preferable to dispose the forefront of the front side tubular portion 142 at a rear end of the imaging marker 132 or at a position proximate to the rear end of the imaging marker. It is preferable that the front side tubular portion 42 does not coat the imaging marker 132. It is preferable to fix the front side tubular portion 142 to the inner tube 103 by means of heat seal.

As materials to be used to form the balloon part 104 and the front side sleeve portion 120, thermoplastic synthetic resin having elasticity is used. More specifically, polyurethane elastomer and urethane elastomer, olefin elastomer (for example, polyethylene elastomer, polypropylene elastomer), polyester such as polyethylene terephthalate, soft polyvinyl chloride, polyamide elastomer and amide elastomer (for example, polyamide elastomer), fluororesin elastomer, and synthetic resin elastomer such as an ethylene-vinyl acetate copolymer are preferable. Thermoplastic polyurethane elastomer (for example, thermoplastic aromatic polyurethane elastomer, thermoplastic aliphatic polyurethane elastomer) is especially preferable. Examples of the thermoplastic polyurethane elastomer include thermoplastic aromatic and aliphatic polyurethane elastomers.

As materials to be used to form the balloon part 104 and the front side sleeve portion 120, materials having a glass transition point not more than 0 degree C. are favorable and those having the glass transition point not more than −10 degree C. are especially favorable. Materials having a softening point (Vicat softening point) not less than 70 degree C. are favorable and those having the softening point in a range from 80 degree C. to 130 degree C. are especially favorable. The balloon part 104 having higher flexibility than the inner tube 103 and the front side sleeve portion 120 is preferable.

In the balloon part 104 of this embodiment, an end portion of the front side tubular portion 142 at an expandable portion side thereof and an end portion 174 of the front side sleeve portion 120 at the expandable portion side thereof have a small diameter respectively. It is preferable to set the length of the front side sleeve portion 120 larger than the axial length of the front side tubular portion and extend the front side sleeve portion rearward. By so doing, the overall length of the balloon is allowed to be long. Thus it is possible to form a long low profile portion at the front side portion of the catheter.

Figure 10:
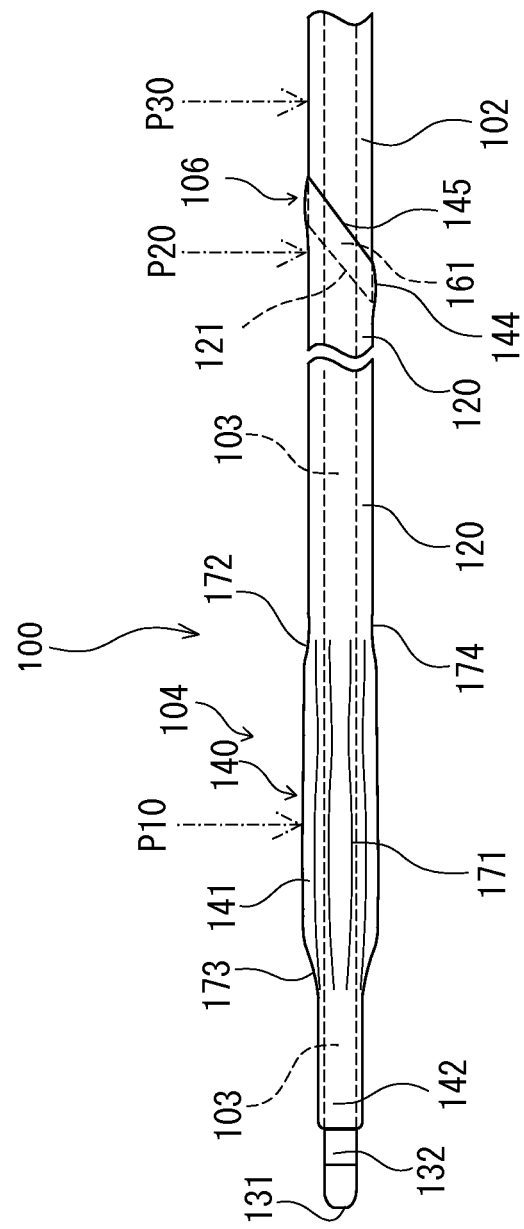
FIG. 10 is an enlarged outside view of a front end portion of the balloon catheter shown in FIG. 9.

As shown in FIGS. 10 and 11, the front side sleeve portion 120 has a non-expandable tubular portion (in other words, sleeve portion) extended in a predetermined length toward the rear end of the outer tube part. The front side sleeve portion 120 has a tilted rear end surface 145 oblique to the central axis of the tubular portion. The front side sleeve portion 120 of the outer tube part and the front end portion of the outer tube main body 102 which is described later tilt to the central axis of the outer tube main body 102 and are fixed to each other at the belt-shaped tilted annular fixing portion 106 air-tightly formed.

In the balloon part 104, the outer diameter (outer diameter when the expandable portion is restored to molded mode) of the expandable portion 141 is set to favorably 0.9 to 2.1 mm and especially favorably 0.9 to 1.0 mm. When the expandable portion expands, its outer diameter (expandable outer diameter) is set to favorably 3.0 to 15.0 mm and especially favorably 4.0 to 8.0 mm. The length of the expandable portion 141 is set to favorably 3.5 to 14.5 mm and especially favorably 4.0 to 5.5 mm. The stretch degree of the expandable portion in its radial direction is set to preferably 300 to 900%. The stretch degree of the expandable portion in its axial direction is set to preferably 200 to 350%.

The outer diameter of the front side tubular portion 142 is set to favorably 0.6 to 1.9 mm and especially favorably 0.7 to 0.9 mm. The length of the front side tubular portion is set to favorably 1.0 to 3.0 mm and especially favorably 1.5 to 2.5 mm.

The expandable portion 141 of the balloon part 104 is thinner than the front side tubular portion 142 and the front side sleeve portion 120. It is favorable to set the thickness of the expandable portion 141 smaller than that of the front side sleeve portion 120 and that of the front side tubular portion 142 by 0.03 to 0.18 mm and especially favorable to set the thickness thereof smaller than that of the front side sleeve portion and that of the front side tubular portion by 0.04 to 0.11 mm. It is favorable to set the thickness of the front side sleeve portion 120 and that of the front side tubular portion 142 to 0.07 to 0.20 mm and especially favorable to set the thickness of the front side sleeve portion and that of the front side tubular portion to 0.08 to 0.15 mm.

In the catheter 100 of this embodiment, the balloon part 104 is fixed to a shaft portion with the balloon part 104 being axially stretched. Therefore, as shown in FIGS. 10 and 11, the balloon part 104 is axially stretched a little. Thus there is a further decrease in the diameter of the expandable portion configured in the diameter-decreased mode.

In the balloon catheter 100 of the present invention, the three-point bending load value A10 of the expandable portion (P10 in FIGS. 10 and 11, in this example, the central portion of the expandable portion where the marker is not positioned) of the balloon per unit deflection and the three-point bending load value A20 of the fixed portion (P20 in FIGS. 10 and 11) per unit deflection where the rear end portion of the front side sleeve portion and the front end portion of the outer tube main body are fixed to each other are set to A10<A20. The difference between the three-point bending load value A10 (P10 in FIGS. 10 and 11) and the three-point bending load value A20 (P20 in FIGS. 10 and 11) is set to not more than 50 mN/mm.

As described above, in the balloon catheter of the present invention, the three-point bending load value A20 is larger than the three-point bending load value A10, and the difference between the three-point bending load value A10 and the three-point bending load value A20 is set to not more than 50 mN/mm. Therefore, in the front side region of the catheter from the front end thereof to the fixing portion where the front side sleeve portion and the outer tube main body are fixed to each other, the flexibility of the front side region becomes lower stepwise from its front end to its rear end. In other words, the flexibility of the front side region becomes stepwise harder. Therefore, kink hardly occurs in the front end portion (flexibility change region) of the catheter. Further, because there is little difference in the flexibility (hardness) at the front side (flexibility change region) of the catheter where there is a change in the flexibility, the catheter is capable of passing through a curved portion of a blood vessel to a high extent. Therefore, the balloon catheter of the present invention can be inserted into lumens with a high degree of operability.

It is preferable to set the three-point bending load value A10 (P10 of FIGS. 10 and 11) to not more than 50 mN/mm.

It is especially preferable to set the three-point bending load value A10 to not more than 50 mN/mm. It is preferable to set the three-point bending load value A20 (P20 of FIGS. 10 and 11) to not more than 100 mN/mm. It is preferable to set the three-point bending load value of the front side sleeve portion 120 of the outer tube part positioned between P10 of FIGS. 10 and 11 and P20 of FIGS. 10 and 11 larger than the three-point bending load value A10 and smaller than the three-point bending load value A30. In the balloon catheter where the three-point bending load values are set as described above, kink hardly occurs to a lower extent, and the catheter the catheter has high performance in passing through the blood vessel.

It is preferable to set the three-point bending load value A30 (P30 of FIGS. 10 and 11) per unit deflection at a portion of the outer tube main body 102 disposed at the side proximal from the fixing portion 106 of the outer tube main body 102 larger than the three-point bending load value A20 (P20 of FIGS. 10 and 11). It is preferable to set the difference between the three-point bending load value A30 (P30 of FIGS. 10 and 11) and the three-point bending load value A20 (P20 of FIGS. 10 and 11) to not more than 300 mN/mm. In the balloon catheter where the three-point bending load values are set as described above, in the front side region of the catheter from the front end thereof to the front end portion of the outer tube main body, the flexibility becomes stepwise lower from the front to rear sides of the front side region. In other words, the flexibility of the front side region becomes stepwise harder from the front to rear sides thereof. Therefore, kink hardly occurs in the front side region including the front end portion of the outer tube main body. Further because the portion of the catheter proximal from the fixing portion 106 of the outer tube main body 102 is hard to some extent, the transmissibility of a pressing force applied to the proximal end of the catheter is favorable.

It is preferable to set the three-point bending load value A30 (P30 of FIGS. 10 and 11) to not more than 350 mN/mm. It is preferable to set the difference between the three-point bending load values A20 and A30 to not more than 300 mN/mm.

It is favorable that the balloon catheter of the present invention can be inserted into a guiding catheter having an inner diameter of 1.1 mm and especially favorable that it can be inserted into the guiding catheter having an inner diameter of 0.95 mm. In the balloon catheter 100 of the present invention, the three-point bending load value A20 is larger than the three-point bending load value A10, and the difference between the three-point bending load values A10 and A20 is set to not more than 50 mN/mm. Therefore, the balloon catheter of the present invention has a high degree of insertion operability, although it has a small diameter. By forming the catheter having such a small diameter, it is possible to insert the catheter into lumens (into blood vessels) having a small diameter. In the balloon catheter of the present invention, it is preferable that a guide wire having an outer diameter of 0.36 mm can be inserted into the inner tube and it is especially preferable that a guide wire having an outer diameter of 0.53 mm can be inserted into the inner tube. By setting the inner diameter of the inner tube to such an extent, it is possible to use the guide wire which has a thickness to some extent and is capable of displaying a sufficient guide function. Thereby it is easy to insert the catheter into lumens (into blood vessels).

In the balloon catheter of this embodiment, a fixing portion 106 at which the rear end of the front side sleeve portion 120 and the front end portion of the outer tube main body 102 are joined to each other is formed as the tilted annular fixing portion (in other words, tilted annular fixing portion). The three-point bending load value A20 (P20 of FIGS. 10 and 11) indicates the hardness of the tilted annular fixing portion. In other words, the three-point bending load value A20 indicates a load value measured when a load is vertically applied to the central portion of the annular fixing portion with a pressurizing rod.

Figure 13:
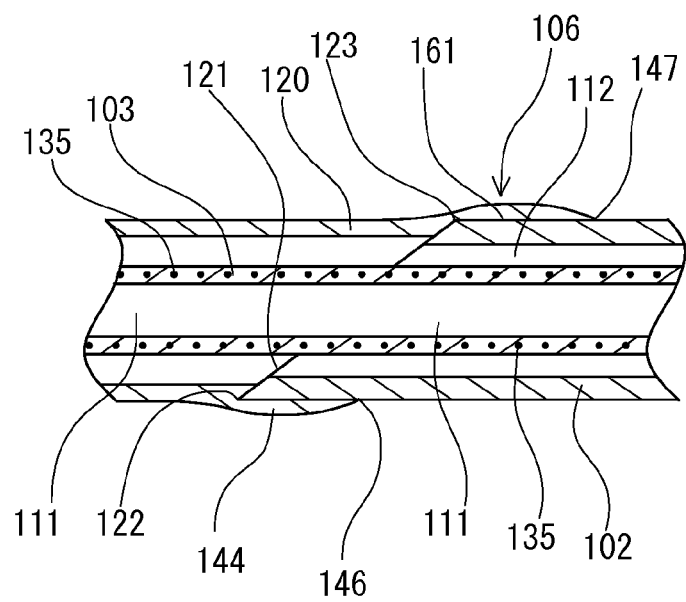
FIG. 13 is an explanatory view for explaining a firmly fixing portion where a rear end portion of a balloon of the balloon catheter shown in FIG. 9 and a front end portion of the outer tube thereof are firmly fixed to each other.

By using FIGS. 13 and 15, the fixing portion 106 at which the front side sleeve portion 120 of the balloon catheter of this embodiment and the front end portion of the outer tube main body 102 are joined to each other is described below.

As described above, the outer tube main body 102 has the tilted front end surface 121 oblique to the central axis of the outer tube main body 102 at the front end portion thereof. The balloon part 104 has the tilted rear end surface 145 to the central axis of the front side sleeve portion 120 at the rear end portion 144 thereof. A portion of the front end portion of the outer tube main body 102 and a portion of the rear end of the front side sleeve portion 120 axially overlap each other. The balloon catheter has the belt-shaped air-tightly formed tilted annular fixing portion 106 disposed at the portion where the front end portion of the outer tube main body 102 and the rear end portion of the front side sleeve portion 120 overlap each other and tilted to the central axis of the outer tube main body 102. The outer tube main body 102 and the balloon part 104 are fixed to each other at the tilted annular fixing portion 106. Because the front side sleeve portion 120 of the outer tube part is more flexible than the front end portion of the outer tube main body 102, the portion where the tilted annular fixing portion 106 is formed becomes higher in the flexibility thereof from its rear end to its front end. Therefore, in the neighborhood of the front end portion of the outer tube main body 102, a change point where the property changes abruptly is not formed. Thus the neighborhood of the front end portion of the outer tube main body 102 is prevented from generating kink and has a preferable deformability.

In the balloon catheter 100 of this embodiment, the rear end of the front side sleeve portion 120 is formed as a diameter-increased portion (in other words, tilted diameter-increased portion, tilted expandable portion). The rear end surface 145 of the front side sleeve portion 120 forms the tilted rear end surface tilted at a predetermined angle to the central axis of the front side sleeve portion 120 (outer tube main body 102). The front end portion of the outer tube main body 102 enters into the diameter-increased rear end portion 144. The entry portion forms the portion where the front end portion of the outer tube main body 102 and the rear end portion of the front side sleeve portion 120 overlap each other. The outer diameter of the outer tube main body 102 is almost equal to that of the front side sleeve portion 120 of the outer tube part. The rear end of the front side sleeve portion 120 is in a bulged state.

Figure 14:
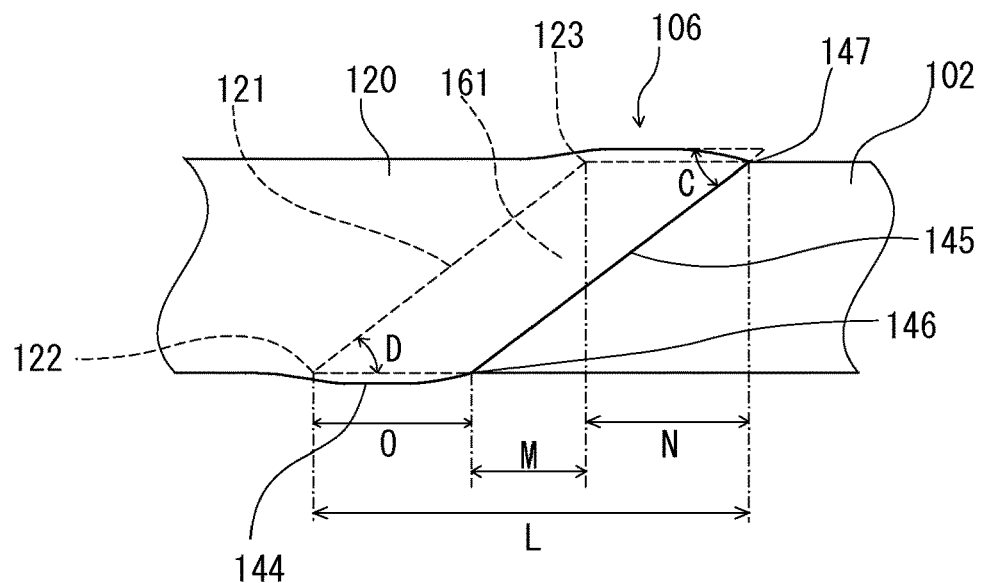
FIG. 14 is an explanatory view for explaining the firmly fixing portion where the rear end portion of a balloon of the balloon catheter shown in FIG. 9 and the front end portion of the outer tube thereof are firmly fixed to each other.

In the balloon catheter 100 of this embodiment, as shown in FIG. 14, the tilted rear end surface 145 of the front side sleeve portion 120 and the tilted front end surface 121 of the outer tube main body 102 are almost parallel to each other or the difference between the tilt angle of the tilted rear end surface of the front side sleeve portion which makes with the central axis of the outer tube and the tilt angle of the tilted front end surface of the outer tube main body which makes with the central axis of the outer tube is set to not more than 44 degrees and preferably not more than 20 degrees. Like the balloon catheter shown in FIG. 14, it is preferable to set a tilt angle D of the tilted front end surface 121 of the outer tube main body 102 which makes with the central axis of the outer tube main body 102 larger than a tilt angle C of the tilted rear end surface 145 of the front side sleeve portion 120 (outer tube main body 102) which makes with the central axis of the front side sleeve portion 120 (outer tube main body 102). It is preferable to set the tilt angle C of the tilted rear end surface 145 of the front side sleeve portion 120 which makes with the central axis of the front side sleeve portion 120 (outer tube main body 102) to 20 to 30 degrees and especially favorably 22 to 28 degrees. It is preferable to set the tilt angle D of the tilted front end surface 121 of the outer tube main body 102 which makes with the central axis of the outer tube main body 102 to 30 to 45 degrees and especially favorably 35 to 43 degrees.

The front end portion of the outer tube main body 102 which has entered into the diameter-increased rear end portion 144 of the front side sleeve portion 120 is air-tightly fixed to the balloon part 104 and forms the belt-shaped tilted annular fixing portion 106. The tilted annular fixing portion 106 has an annular firmly fixing portion 161. The fixing portion 161 is formed on the entire inner surface of the proximal portion 144 of the front side sleeve portion 120 which contacts the outer surface of the front end portion of the outer tube main body 102 of the tilted annular firmly fixing portion 106. As described later, a non-fixing portion which does not adversely affect the airtightness between both surfaces may be provided.

It is preferable that the annular firmly fixing portion 161 is almost uniform or becomes gradually larger toward its rear end in its width. In the balloon catheter 100 of this embodiment, as shown in FIG. 14, the annular firmly fixing portion 161 becomes gradually larger toward its rear end in its width.

In the balloon catheter 100 of this embodiment shown in FIG. 14, an imaginary line connecting a front end 122 of the tilted front end surface 121 of the outer tube main body 102 and a front end 146 of the tilted rear end surface 145 of the front side sleeve portion 120 is almost parallel with the central axis of the outer tube main body 102. That is, the front end 122 of the tilted front end surface 121 of the outer tube main body 102 is positioned forward from the front end 146 of the tilted rear end surface 145 of the front side sleeve portion 120. Similarly an imaginary line connecting a rear end 123 of the tilted front end surface 121 of the outer tube main body 102 and a rear end 147 of the tilted rear end surface 145 of the front side sleeve portion 120 is almost parallel with the central axis of the outer tube main body 102. That is, the rear end 123 of the tilted front end surface 121 of the outer tube main body 102 is positioned forward from the rear end 147 of the tilted rear end surface 145 of the front side sleeve portion 120. Therefore, a portion small in width is not formed at the annular firmly fixing portion 161.

In this embodiment, the front end 146 of the tilted rear end surface 145 of the front side sleeve portion 120 is positioned forward from the front end 123 of the tilted front end surface 121 of the outer tube main body 102. Therefore, the property of the tilted annular fixing portion 106 continuously changes. Because the front side sleeve portion 120 of the outer tube part has higher flexibility than the front end portion of the outer tube main body 102, the portion where the tilted annular fixing portion 106 is formed becomes gradually higher from its rear end to its front end in its flexibility. In the tilted annular fixing portion 106 of this embodiment, a portion where the rear end portion 144 of the front side sleeve portion 120 covers the front end portion of the outer tube main body 102 increases from the rear end of the tilted annular fixing portion 106 to the front end thereof. When the rear end 144 of the front side sleeve portion 120 passes the rear end 123 of the tilted front end surface 121, the rear end of the front side sleeve portion 120 continues to increases in the sectional area of a section thereof orthogonal to the central axis of the outer tube main body. But the front end portion of the outer tube main body 102 decreases in the sectional area of a section thereof orthogonal to the central axis of the outer tube main body. The section of the rear end portion 144 of the front side sleeve portion 120 becomes annular at the front end 146 of the tilted surface 145 disposed at the rear end of the front side sleeve portion 120. At the front side of the front end 146, the front end portion of the outer tube main body 102 decreases in the sectional area thereof and terminates at the front end 122. That is, in the entire tilted annular fixing portion 106 of the balloon catheter of this embodiment, neither the rear end portion of the front side sleeve portion 120 nor the front end portion of the outer tube main body 102 has an annular portion on a cut surface orthogonal to the central axis of the outer tube main body 102.

It is preferable to set a distance O between the front end 122 of the outer tube main body 102 shown in FIG. 14 and the front end 146 of the tilted rear end surface 145 of the front side sleeve portion 120 to 0.5 to 2.0 mm and especially preferable to set the distance O to 0.6 to 1.5 mm. It is preferable to set a distance N between the rear end 123 of the tilted front end surface 121 of the outer tube main body 102 and the rear end 147 of the tilted rear end surface 145 of the front side sleeve portion 120 to 0.5 to 4.0 mm and especially preferable to set the distance N to 0.6 to 1.0 mm. It is preferable to set an axial length L (in other words, the distance L between the front end 122 of the outer tube main body 102 and the rear end 147 of the tilted rear end surface 145 of the front side sleeve portion 120) to 2.0 to 8.0 mm and especially preferable to set the distance L to 2.3 to 3.5 mm. It is preferable to set a distance M between the rear end 123 of the tilted front end surface 121 of the outer tube main body 102 and the front end 146 of the tilted rear end surface 145 of the front side sleeve portion 120 to 0.6 to 2.5 mm and especially preferable to set the distance N to 0.8 to 1.5 mm.

The distance M between the rear end 123 of the tilted front end surface 121 of the outer tube main body 102 and the front end 146 of the tilted rear end surface 145 of the front side sleeve portion 120 may be set to zero. That is, like an embodiment shown in FIG. 15, the rear end 123 of the tilted front end surface 121 of the outer tube main body 102 and the front end 146 of the tilted rear end surface 145 of the front side sleeve portion 120 may be coincident with each other in the axial direction of the outer tube main body 102. It is preferable that the rear end 123 of the tilted front end surface 121 of the outer tube main body 102 is not located at a front side of the front end 146 of the tilted rear end surface 145 of the front side sleeve portion 120.

Figure 15:
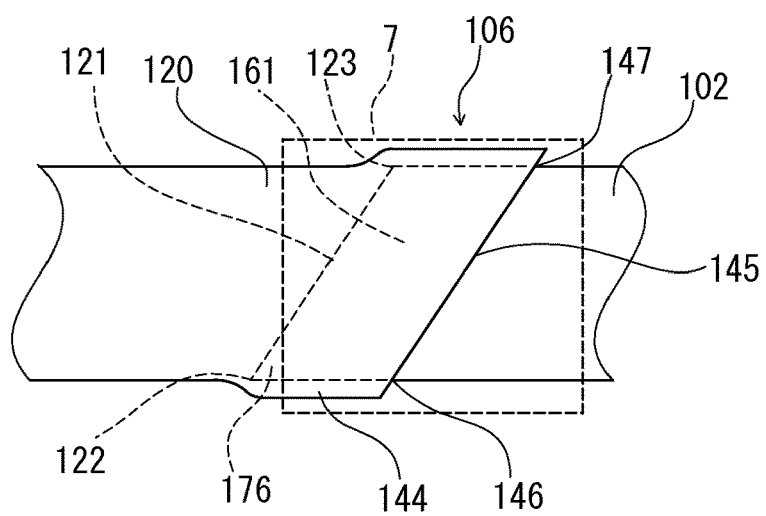
FIG. 15 is an explanatory view for explaining the firmly fixing portion where the rear end portion of a balloon of the balloon catheter shown in FIG. 9 and the front end portion of the outer tube thereof are firmly fixed to each other.

As shown in FIG. 15, the tilted annular fixing portion 106 is formed by inserting the front end portion of the outer tube main body 102 into the rear end of the front side sleeve portion 120, fitting a heat-shrinkable tube on an overlapped portion and on front and rear portions of the overlapped portion in a length of about 2 mm, and heating the outer surface of the heat-shrinkable tube by using a heating member 7 so as to fuse both to each other. The outer edge of the tilted front end surface of the outer tube main body 102 is edgeless and rounded owing to the fusion. As shown in FIG. 15, the fusion process may be performed in such a way that the front end portion of the tilted front end surface 121 of the outer tube main body 102 is not directly heated. By so doing, at the front end of the outer tube main body 102, it is possible to form a non-fusion portion 176 which does not fuse to the rear end of the front side sleeve portion 120 or form a weak fusion portion. By forming such a weak fusion portion, the rear end of a portion (non-overlapped portion) of the front side sleeve portion 120 where the outer tube main body 102 is not present is not compressed by heated heat-shrinkable tube. Thus a thin portion is prevented from being formed at a sealing portion.

Figure 16:
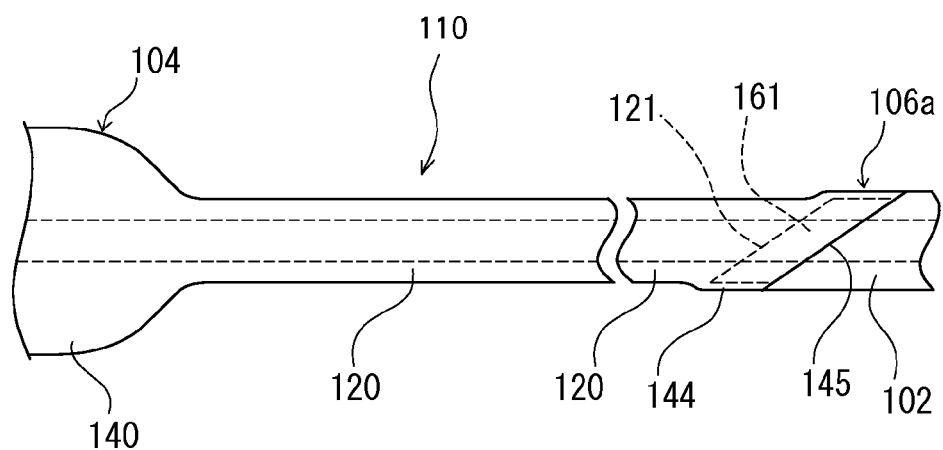
FIG. 16 is an enlarged outlook view of a neighborhood of a firmly fixing portion where a rear end portion of a balloon of a balloon catheter of another embodiment of the present invention and a front end portion of an outer tube thereof are firmly fixed to each other.
Figure 17:
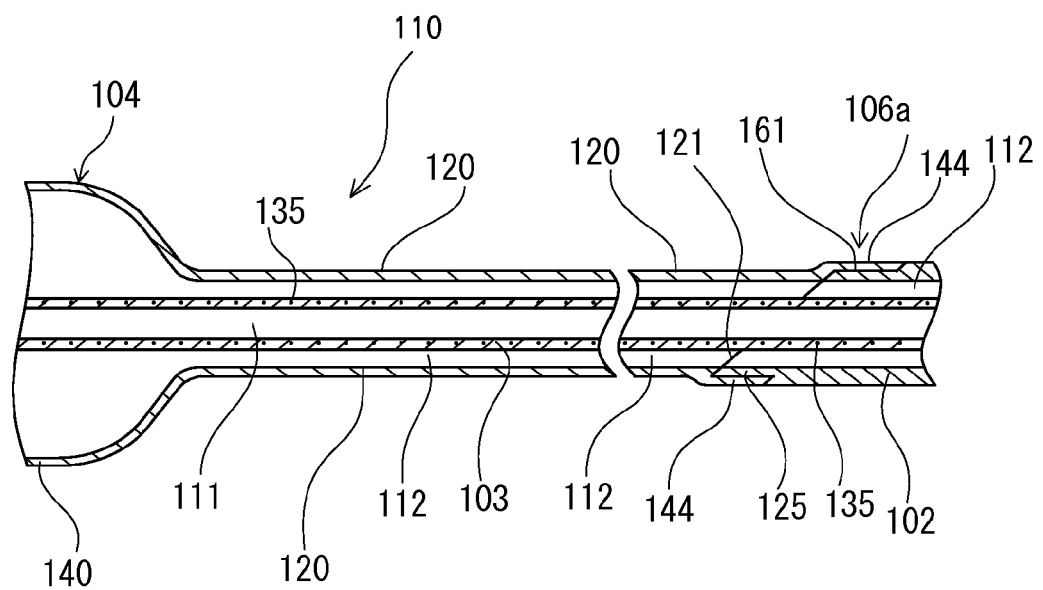
FIG. 17 is a vertical sectional view of FIG. 16.
Figure 18:
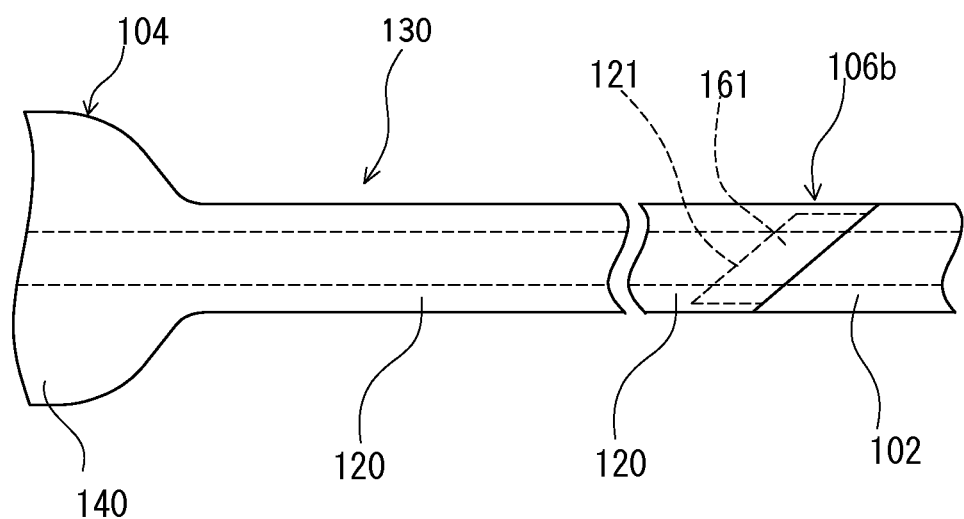
FIG. 18 is an enlarged outlook view of a neighborhood of a firmly fixing portion where a rear end portion of a balloon of a balloon catheter of another embodiment of the present invention and a front end portion of an outer tube thereof are firmly fixed to each other.
Figure 19:
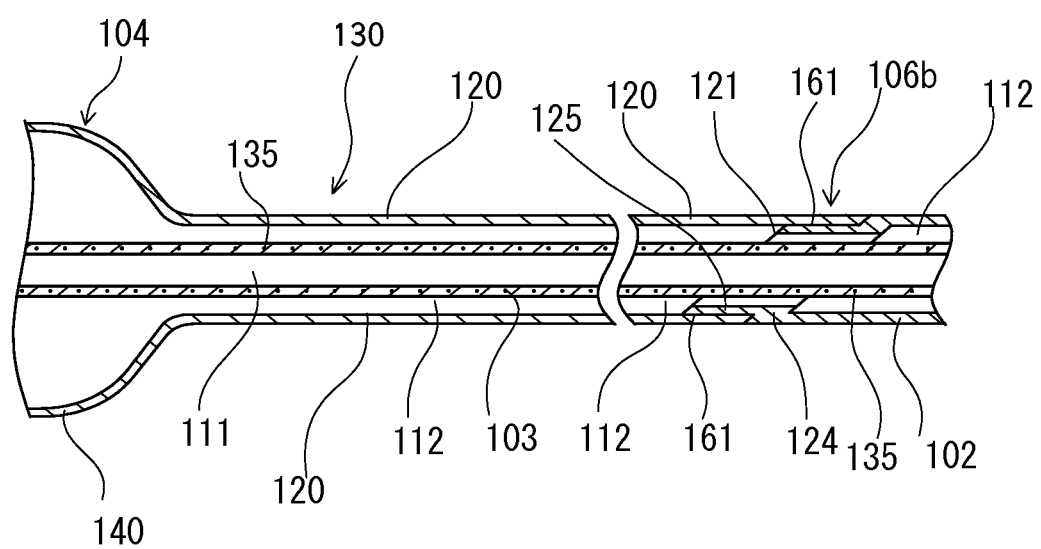
FIG. 19 is a vertical sectional view of FIG. 18.

The mode of joining the rear end of the front side sleeve portion 120 and the front end portion of the outer tube main body 102 to each other is not limited to the above-described one, but may be of a type a balloon catheter 110 of an embodiment shown in FIGS. 16 and 17 has.

In the balloon catheter 110 of this embodiment, the front end portion of the outer tube main body 102 is formed as a tilted small diameter portion 125. The tilted front end surface 121 is formed at a front end of the tilted small diameter portion. The outer diameter of the rear end of the front side sleeve portion 120 is almost equal to that of a portion of the outer tube main body disposed proximally from the tilted small diameter portion of the outer tube main body 102. A tilted annular fixing portion 106a is formed by inserting the tilted small diameter portion of the outer tube main body 102 into the tilted rear end portion 144 of the front side sleeve portion 120 and fixing the tilted small diameter portion to the tilted rear end portion 144. In the balloon catheter 110, a part of the rear end portion of the front side sleeve portion 120 is formed as the tilted expandable portion. A part of the front side sleeve portion 120 rearward from the tilted expandable portion is extended to the rear end portion of the outer tube main body 102 in almost an equal outer diameter. The mode of joining the rear end of the front side sleeve portion 120 and the front end portion of the outer tube main body 102 to each other may be of a type a balloon catheter 130 of an embodiment shown in FIGS. 18 and 19 has.

In the balloon catheter 130 of this embodiment, the rear end of the front side sleeve portion 120 is formed not as the tilted diameter-increased portion, but as an obliquely terminated portion formed by extending the front side sleeve portion rearward. The front end portion of the outer tube main body 102 has the tilted small diameter portion 125 and a thick portion 124 continuous therewith. The tilted front end surface 121 is formed at the front end of the tilted small diameter portion 125. The outer diameter of a part of the outer tube main body 102 disposed proximally from the tilted small diameter portion thereof is set almost equally to that of the front side sleeve portion 120 and that of the rear end portion thereof. A tilted annular fixing portion 106b is formed by inserting the tilted small diameter portion 125 of the outer tube main body 102 into the tilted rear end portion of the front side sleeve portion 120 and fixing thereto. In the balloon catheter 130, a part of the front side sleeve portion 120 disposed rearward from the expandable portion 141 is extended to the rear end portion of the outer tube main body 102 in almost a uniform outer diameter. The balloon catheter 130 is so constructed that it does not have a level-different portion at a portion where the balloon part 104 exposed to the outside and the outer tube main body 102 are joined to each other.

Figure 20:
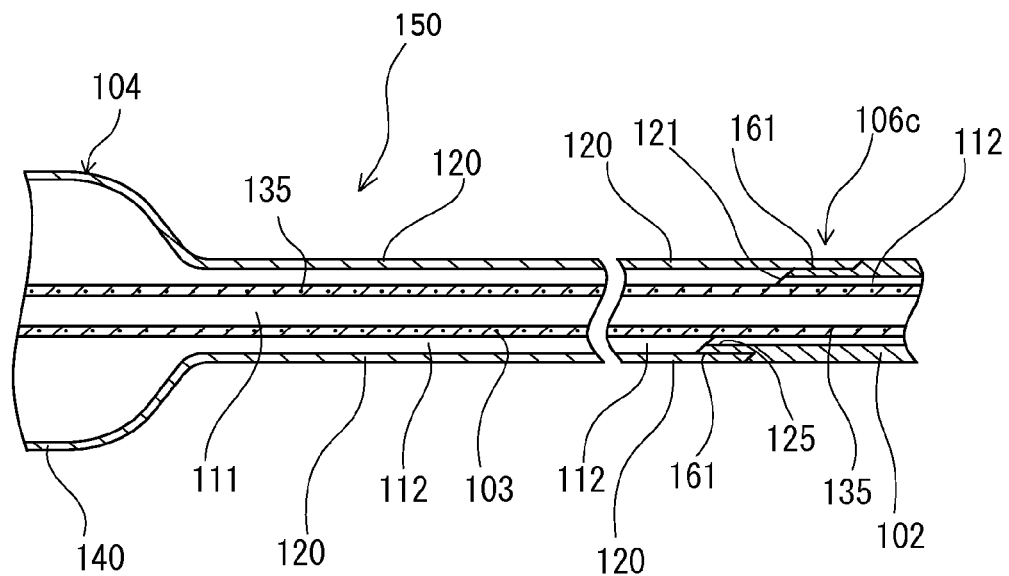
FIG. 20 is an enlarged sectional view of a neighborhood of a firmly fixing portion where a rear end portion of a balloon of a balloon catheter of another embodiment of the present invention and a front end portion of an outer tube thereof are firmly fixed to each other.

Like a balloon catheter 150 shown in FIG. 20, the outer tube main body 102 may be extended to the rear end portion of the balloon catheter in an inner diameter entirely equal to that of the tilted small diameter portion 125. A tilted annular fixing portion 106c is formed by inserting the tilted front end portion of the outer tube main body 102 into the tilted rear end portion of the front side sleeve portion 120 and fixing thereto.

Figure 21:
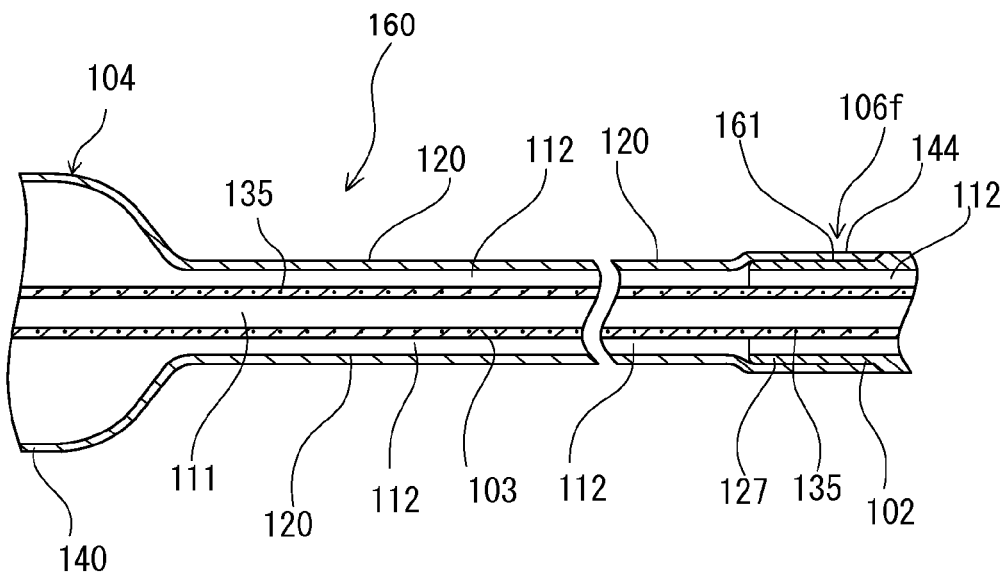
FIG. 21 is an enlarged sectional view of a neighborhood of a firmly fixing portion where a rear end portion of a balloon of a balloon catheter of another embodiment of the present invention and a front end portion of an outer tube thereof are firmly fixed to each other.

The mode of joining the rear end of the front side sleeve portion 120 and the front end portion of the outer tube main body 102 to each other is not limited to the above-described ones, but may be of a type a balloon catheter 160 of an embodiment shown in FIG. 21 has.

In the balloon catheter 160 of this embodiment, the front end portion of the outer tube main body 102 is formed not as the tilted portion of the above-described embodiment, but as a thin small diameter portion 127. The front end portion of the outer tube of this embodiment is also formed as the easily deformable front end portion more deformable than other portions of the outer tube.

The inner diameter of the rear end of the front side sleeve portion 120 is almost equal to the outer diameter of the thin small diameter portion 127 of the outer tube main body 102. A tilted annular fixing portion 106f is formed by inserting the tilted small diameter portion 127 of the outer tube main body 102 into the rear end of the front side sleeve portion 120 and fixing thereto. In the balloon catheter 160, the rear side portion of the front side sleeve portion 120 is formed as the diameter-increased portion and covers the thin small diameter portion 127 of the outer tube main body 102. The outer diameter of the rear end of the front side sleeve portion 120 is almost equal to that of a portion of the outer tube main body 102 disposed rearward from the thin small diameter portion 127 thereof. The balloon catheter 160 is so constructed that it does not have a level-different portion and a gap at a portion where the rear end of the front side sleeve portion 120 exposed to the outside and the outer tube main body 102 are joined to each other.

Figure 22:
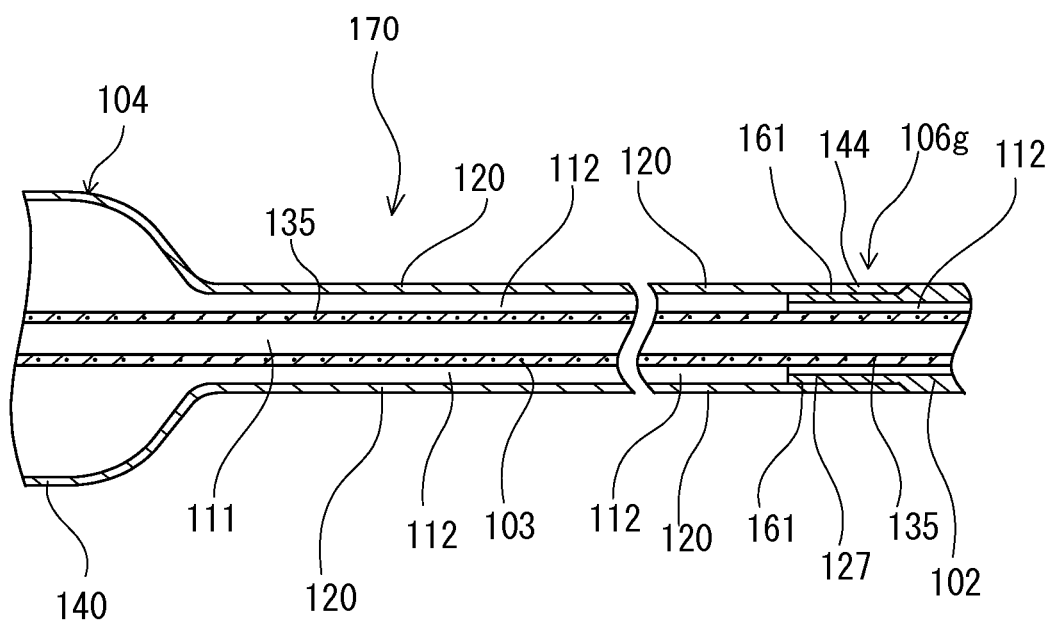
FIG. 22 is an enlarged sectional view of a neighborhood of a firmly fixing portion where a rear end portion of a balloon of a balloon catheter of another embodiment of the present invention and a front end portion of an outer tube thereof are firmly fixed to each other.

The mode of joining the rear end of the front side sleeve portion 120 and the front end portion of the outer tube main body 102 to each other may be of a type a balloon catheter 170 of an embodiment shown in FIG. 22 has.

In the balloon catheter 170 of this embodiment, as with the balloon catheter 160, the front end portion of the outer tube main body 102 is formed not as the tilted portion of the above-described embodiment, but as the thin small diameter portion 127. The front end portion of the outer tube of this embodiment is also formed as the easily deformable front end portion more deformable than other portions of the outer tube.

Unlike the balloon catheter 160, the rear end of the front side sleeve portion 120 is not formed as the diameter-increased portion. Thus the front side sleeve portion 120 of the outer tube part is entirely extended in almost a uniform inner diameter and a uniform outer diameter. The outer diameter of the thin small diameter portion 127 at the front end portion of the outer tube main body 102 is almost equal to the inner diameter of the front side sleeve portion 120 of the outer tube part.

A tilted annular fixing portion 106g is formed by inserting the thin small diameter portion 127 of the outer tube main body 102 into the rear end of the front side sleeve portion 120 and fixing thereto. The balloon catheter 170 is so constructed that it does not have a level-different portion at a portion where the balloon part 104 exposed to the outside and the outer tube main body 102 are joined to each other.

Figure 12:
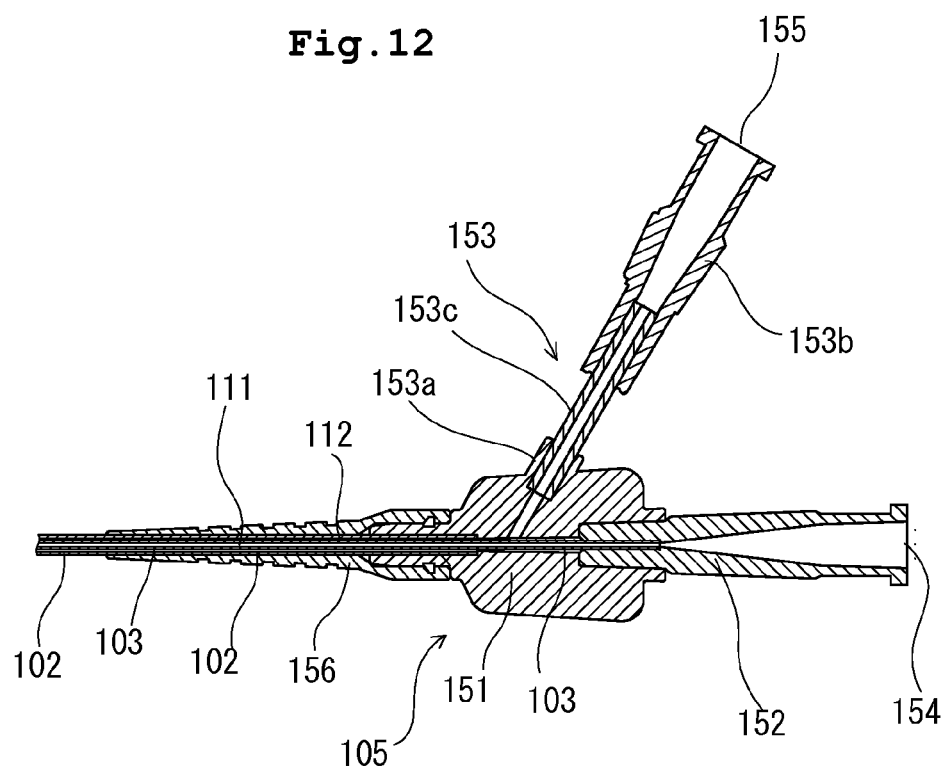
FIG. 12 is an enlarged vertical sectional view of a proximal part of the balloon catheter shown in FIG. 9.

As shown in FIG. 12, the branch hub 105 has an inner tube hub 152 which has a first open portion 154 communicating with the first lumen 111 and is fixed to the rear end portion of the inner tube 103 and an outer tube hub 151 which has a second open portion 155 communicating with the second lumen 112 and forming an injection port 153 and is fixed to the rear end portion of the outer tube main body 102. The outer tube hub 151 and the inner tube hub 152 are fixed to each other. The outer tube hub 151 and the inner tube hub 52 are fixed to each other by inserting the inner tube 103 into a rear end of the outer tube hub 151 mounted on the proximal portion of the outer tube main body 102 from the front end of the inner tube 103 and joining. The branch hub 105 is provided with a bending prevention tube 156 covering the proximal portion of the outer tube main body 102 and a front end portion of the branch hub 105. The injection port 153 is formed of a branch port 153a extended from a side wall of the outer tube hub 151, an injection port hub 153b, and a connection tube 153c connecting the branch port 153a and the injection port hub 153b to each other. As materials to be used to form the branch hub, it is possible to suitably use thermoplastic resin such as polycarbonate, polyamide, polysulfone, polyarylate, and a methacrylate-butylene-styrene copolymer. As the connection tube, a flexible synthetic resin or a soft synthetic resin is used.

The construction of the balloon catheter is not limited to the above-described ones, but the balloon catheter may have a guide wire insertion opening communicating with a guide wire lumen at an intermediate portion (rearward from the tilted annular fixing portion 106) thereof.

It is preferable to apply the balloon catheter of the present invention to a medicine administering catheter provided with a blood vessel occluding function.

INDUSTRIAL APPLICABILITY

The balloon catheter of the present invention has the following features.

A balloon catheter has an inner tube having a first lumen, an outer tube part provided coaxially with the inner tube and forming a second lumen between the outer tube part and an outer surface of the inner tube, and a balloon part, a front end portion of which is fixed to a front end portion of the inner tube and an inside of which communicates with the second lumen. The balloon part has a bulged portion, having an expansion forming mode formed in advance, which is elastically deformable beyond the expansion forming mode by a balloon expansion liquid injected thereinto. The outer tube part has a front side sleeve portion which is extended from a rear end portion of the bulged portion of the balloon part toward a proximal end of the outer tube part, is formed integrally with the balloon part by using the same material as that to be used for the balloon part, and is substantially non-expandable.

The balloon part has the expansion forming mode formed in advance. Until before the expansion forming mode is formed, the balloon part is expanded by a very low pressure of the liquid injected thereinto and is capable of elastically deforming beyond the expansion formation mode. Thereby the balloon part closely contacts the inner wall of a blood vessel and is capable of occluding the blood vessel. In addition, because the outer tube part has the front side sleeve portion formed integrally with the balloon part, the catheter does not have an abrupt change in the property in the region (front side region) from the front end of the catheter to the front side sleeve portion of the outer tube, has little generation of kink in the front side region thereof, and favorably passes through a curved portion of the blood vessel. The bulged part is elastically deformable, whereas the front side sleeve portion is substantially non-expandable. Thus when the balloon expands, the diameter of the front side sleeve portion does not increase. Therefore, the operability of the catheter does not deteriorate.

The present invention may be embodied as described below.

(2) A balloon catheter according to the above (1), wherein said outer tube part is formed entirely integrally with said balloon part by using the same material as that to be used for said balloon part.

(3) A balloon catheter according to the above (1), wherein said outer tube part comprises said front side sleeve portion and an outer tube main body, a front end portion of which is fixed to a rear end portion of said front side sleeve portion.

(4) A balloon catheter according to any one of these above (1) through (3), wherein said bulged portion of said balloon part has an elastically deformable portion, a front side tapered portion, provided forward from said elastically deformable portion, which decreases toward a front end thereof in a diameter thereof and is substantially elastically undeformable, and a rear side tapered portion, provided rearward from said elastically deformable portion, which decreases toward a rear end thereof in a diameter thereof and is substantially elastically undeformable.

(5) A balloon catheter according to any one of these above (1) through (4), wherein said balloon catheter is used to occlude a blood vessel.

(6) A balloon catheter according to the above (4) or (5), wherein said front side tapered portion of said balloon part is formed as a thickness change portion which becomes gradually thicker to a front end thereof, and said rear side tapered portion of said balloon part is formed as a thickness change portion which becomes gradually thicker to a rear end thereof.

(7) A balloon catheter according to any one of these above (3) through (6), wherein said outer tube part has an outer tube main body which is extended from a rear end portion of said front side sleeve portion to a proximal end of said balloon catheter and is harder than said front side sleeve portion; a three-point bending load value A1 per unit deflection at said expandable portion of said balloon part, a three-point bending load value A2 per unit deflection at said front side sleeve portion, and a three-point bending load value A3 per unit deflection at a front side portion of said outer tube main body are set to A1<A2<A3; a difference between said three-point bending load value A1 and said three-point bending load value A3 is set to not more than 300 mN/mm; and said three-point bending load value A1 is set to not more than 50 mN/mm.

(8) A balloon catheter according to any one of these above (3) through (7), wherein said outer tube part has an outer tube main body which is extended from a rear end portion of said front side sleeve portion to a proximal end of said balloon catheter and is harder than said front side sleeve portion; a three-point bending load value A1 per unit deflection at said expandable portion of said balloon part and a three-point bending load value A4 per unit deflection at a boundary portion between said front side sleeve portion and said outer tube main body are set to A1<A4; a difference between said three-point bending load value A1 and said three-point bending load value A4 is set to not more than 50 mN/mm; and said three-point bending load value A1 is set to not more than 50 mN/mm.

(9) A balloon catheter according to the above (7) or (8), wherein said three-point bending load value A2 is set to not more than 100 mN/mm.

(10) A balloon catheter according to any one of these above (7) through (9), wherein said three-point bending load value A1 is set to not more than 40 mN/mm.

(11) A balloon catheter according to any one of these above (1) through (10), wherein a length of said front side sleeve portion of said outer tube part is set to not less than 2.5 times as long as a length of said expandable portion of said balloon part.

(12). A balloon catheter according to any one of these above (1) through (11), wherein said balloon catheter can be inserted into a guiding catheter having an inner diameter of 1.1 mm; and a guide wire having an outer diameter of 0.53 mm can be inserted into said inner tube.

The invention claimed is:

1. A balloon catheter comprising:
an inner tube having a first lumen;
an outer tube part provided coaxially with said inner tube and forming a second lumen between said outer tube part and an outer surface of said inner tube; and
a balloon part, a front end portion of which is fixed to a front end portion of said inner tube and an inside of which communicates with said second lumen,
said balloon part has a bulged portion, having an expanded configuration formed in advance before introducing balloon expansion liquid into the bulged portion, the bulged portion being elastically deformable beyond said expanded configuration by introducing the balloon expansion liquid into the bulged portion,
said outer tube part has a front side sleeve portion which is extended from a rear end portion of said bulged portion of said balloon part toward a proximal end of said outer tube part, is formed integrally with said balloon part by using the same material as that used for said balloon part, and is substantially non-expandable, the front side sleeve portion possessing a central axis,
the outer tube part including an outer tube main body possessing a front end portion fixed to a rear end portion of the front side sleeve portion, the outer tube main body possessing a central axis,
the front side sleeve portion including a tilted rear end surface oblique to the central axis of the front side sleeve portion,
the outer tube main body including a tilted front end surface oblique to the central axis of the outer tube main body,
the outer tube part including a belt-shaped tilted annular fixing portion formed by fixing an overlapped portion of the rear end portion of the front side sleeve portion and the front end portion of the outer tube main body, and
the belt-shaped tilted annular fixing portion being oblique to the central axis of the front side sleeve portion.

2. The balloon catheter according to claim 1, wherein said outer tube part is formed entirely integrally with said balloon part by using the same material as that used for said balloon part.

3. The balloon catheter according to claim 1, wherein said bulged portion of said balloon part has an elastically deformable portion, a front side tapered portion, provided forward from said elastically deformable portion, which decreases toward a front end thereof in a diameter thereof and is substantially elastically undeformable, and a rear side tapered portion, provided rearward from said elastically deformable portion, which decreases toward a rear end thereof in a diameter thereof and is substantially elastically undeformable.

4. The balloon catheter according to claim 3, wherein said front side tapered portion of said balloon part is formed as a thickness change portion which becomes gradually thicker to a front end thereof, and said rear side tapered portion of said balloon part is formed as a thickness change portion which becomes gradually thicker to a rear end thereof.

5. The balloon catheter according to claim 1, wherein said balloon catheter is configured to occlude a blood vessel.

6. The balloon catheter according to claim 1, wherein said outer tube part has an outer tube main body which is extended from a rear end portion of said front side sleeve portion to a proximal end of said balloon catheter and is less flexible than said front side sleeve portion;
a three-point bending load value A1 per unit deflection at said expandable portion of said balloon part, a three-point bending load value A2 per unit deflection at said front side sleeve portion, and a three-point bending load value A3 per unit deflection at a front side portion of said outer tube main body are set to A1<A2<A3; a difference between said three-point bending load value A1 and said three-point bending load value A3 is set to not more than 300 m N/mm; and
said three-point bending load value A1 is set to not more than 50 m N/mm.

7. The balloon catheter according to claim 1, wherein said outer tube part has an outer tube main body which is extended from a rear end portion of said front side sleeve portion to a proximal end of said balloon catheter and is less flexible than said front side sleeve portion;
a three-point bending load value A1 per unit deflection at said expandable portion of said balloon part and a three-point bending load value A4 per unit deflection at a boundary portion between said front side sleeve portion and said outer tube main body are set to A1<A4;
a difference between said three-point bending load value A1 and said three-point bending load value A4 is set to not more than 50 mN/mm; and
said three-point bending load value A1 is set to not more than 50 m N/mm.

8. The balloon catheter according to claim 6, wherein said three-point bending load value A2 is set to not more than 100 mN/mm.

9. The balloon catheter according to claim 6, wherein said three-point bending load value A1 is set to not more than 40 m N/mm.

10. The balloon catheter according to claim 1, wherein a length of said front side sleeve portion of said outer tube part is set to not less than 2.5 times as long as a length of said bulged portion of said balloon part.

11. The balloon catheter according to claim 1, wherein said balloon catheter is insertable into a guiding catheter having an inner diameter of 1.1 mm; and
a guide wire having an outer diameter of 0.53 mm can be inserted into said inner tube.

12. The balloon catheter according to claim 1, wherein the front side sleeve portion of the outer tube part being more flexible than the front end portion of the outer tube main body, the belt-shaped tilted annular fixing portion possessing a rear end and a front portion having a front end, the front portion of the belt-shaped tilted annular fixing portion possessing a flexibility that increases in a direction toward the front end of the belt-shaped titled annular fixing portion.

13. The balloon catheter according to claim 1, wherein a front end of the tilted rear end surface of the front side sleeve portion is almost parallel with the central axis of the outer tube main body and a rear end of the tilted rear end surface of the front side sleeve portion is almost parallel with the central axis of the outer tube main body.

14. A balloon catheter comprising:
an inner tube including a first lumen; an outer tube part coaxial with the inner tube and forming a second lumen between the outer tube part and an outer surface of the inner tube; and a balloon part possessing a front end portion fixed to a front end portion of the inner tube, the balloon part possessing an inside communicating with the second lumen;
the balloon part including a bulged portion, having an expanded configuration formed in advance before introducing balloon expansion liquid into the bulged portion, the bulged portion being elastically deformable beyond the expanded configuration by introducing the balloon expansion liquid into the bulged portion;
the outer tube part including a front side sleeve portion extending from a rear end portion of the bulged portion of the balloon part toward a proximal end of the outer tube part, the front side sleeve portion being formed integrally with the balloon part by using the same material as that used for the balloon part, the front side sleeve portion being substantially non-expandable and possessing a central axis;
the outer tube part including an outer tube main body possessing a front end portion fixed to a rear end portion of the front side sleeve portion, the outer tube main body possessing a central axis;
the front side sleeve portion including an angled rear end surface oblique to the central axis of the front side sleeve portion;
the outer tube main body including an angled front end surface oblique to the central axis of the outer tube main body;
the outer tube part including an angled annular fixing portion in which a rear end portion of the front side sleeve portion and the front end portion of the outer tube main body axially overlap one another and are fixed to one another;
the front side sleeve portion of the outer tube part being more flexible than the front end portion of the outer tube main body, the angled annular fixing portion possessing a rear end and a front end, and the angled annular fixing portion possessing a flexibility that increases in a direction toward the front end of the angled annular fixing portion; and
the angled annular fixing portion being angled at an angle oblique to the central axis of the front side sleeve portion.

15. The balloon catheter according to claim 14, wherein the outer tube part is formed entirely integrally with the balloon part by using the same material as that used for the balloon part.

16. The balloon catheter according to claim 14, wherein the bulged portion of the balloon part includes an elastically deformable portion, a front side tapered portion forward from the elastically deformable portion and decreasing in outer diameter toward a front end of the front side tapered portion, and a rear side tapered portion rearward from the elastically deformable portion and decreasing in outer diameter toward a rear end of the rear side tapered portion, the front side tapered portion and the rear side tapered portion both being substantially elastically undeformable.

17. The balloon catheter according to claim 14, wherein the front sleeve portion of the outer tube main part is more flexible than the front end portion of the outer tube main body, the angled annular fixing portion possessing a rear end and a front portion having a front end, the front portion of the angled annular fixing portion possessing a flexibility that increases in a direction toward the front end of the angled annular fixing portion.

18. The balloon catheter according to claim 14, wherein a front end of the angled rear end surface of the front side sleeve portion is almost parallel with the central axis of the outer tube main body and a rear end of the angled rear end surface of the front side sleeve portion is almost parallel with the central axis of the outer tube main body.

* * * * *